United States Patent
Daunert et al.

(10) Patent No.: US 11,830,582 B2
(45) Date of Patent: Nov. 28, 2023

(54) METHODS OF DESIGNING NOVEL ANTIBODY MIMETICS FOR USE IN DETECTING ANTIGENS AND AS THERAPEUTIC AGENTS

(71) Applicant: UNIVERSITY OF MIAMI, Miami, FL (US)

(72) Inventors: Sylvia Daunert, Miami, FL (US); Sapna K. Deo, Miami, FL (US); Emre Dikici, Miami, FL (US); Marcello Mascini, Teramo (IT)

(73) Assignee: UNIVERSITY OF MIAMI, Miami, FL (US)

( * ) Notice: Subject to any disclaimer, the term of this patent is extended or adjusted under 35 U.S.C. 154(b) by 659 days.

(21) Appl. No.: 16/441,646

(22) Filed: Jun. 14, 2019

(65) Prior Publication Data
US 2019/0385705 A1 Dec. 19, 2019

Related U.S. Application Data

(60) Provisional application No. 62/684,960, filed on Jun. 14, 2018.

(51) Int. Cl.
  *G01N 33/48* (2006.01)
  *G16B 35/20* (2019.01)
  *C07K 4/00* (2006.01)
  *G16B 15/30* (2019.01)

(52) U.S. Cl.
  CPC ............... *G16B 35/20* (2019.02); *C07K 4/00* (2013.01); *G16B 15/30* (2019.02)

(58) Field of Classification Search
  None
  See application file for complete search history.

(56) References Cited

U.S. PATENT DOCUMENTS

| | | | |
|---|---|---|---|
| 4,946,778 A | 8/1990 | Ladner et al. | |
| 5,225,539 A | 7/1993 | Winter | |
| 5,403,484 A | 4/1995 | Ladner et al. | |
| 5,545,806 A | 8/1996 | Onberg et al. | |
| 5,565,325 A | 10/1996 | Blake | |
| 5,569,825 A | 10/1996 | Lonberg et al. | |
| 5,571,698 A | 11/1996 | Ladner et al. | |
| 5,585,089 A | 12/1996 | Queen et al. | |
| 5,639,641 A | 6/1997 | Pedersen et al. | |
| 5,693,761 A | 12/1997 | Queen et al. | |
| 5,693,762 A | 12/1997 | Queen et al. | |
| 5,702,892 A | 12/1997 | Mulligan-Kehoe | |
| 5,714,352 A | 2/1998 | Jakobobits et al. | |
| 5,780,279 A | 7/1998 | Matthews et al. | |
| 5,821,047 A | 10/1998 | Garrard et al. | |
| 5,824,520 A | 10/1998 | Mulligan-Kehoe | |
| 5,837,500 A | 11/1998 | Ladner et al. | |
| 5,855,885 A | 1/1999 | Smith et al. | |
| 5,858,657 A | 1/1999 | Winter et al. | |
| 5,871,907 A | 2/1999 | Winter et al. | |
| 5,969,108 A | 10/1999 | McCafferty et al. | |
| 6,057,098 A | 5/2000 | Buechler et al. | |
| 6,225,447 B1 | 5/2001 | Winter et al. | |
| 6,265,150 B1 | 7/2001 | Terstappen et al. | |
| 6,551,592 B2 | 4/2003 | Lindhofer et al. | |
| 6,699,843 B2 | 3/2004 | Pietras et al. | |
| 7,355,008 B2 | 4/2008 | Stavenhagen et al. | |
| 7,381,408 B2 | 6/2008 | Mezo et al. | |
| 9,885,050 B2 * | 2/2018 | Koide | C12N 15/62 |
| 2002/0197266 A1 | 12/2002 | Debinski | |
| 2005/0282233 A1 | 12/2005 | Eriksson et al. | |
| 2009/0081230 A1 | 3/2009 | Lanzavecchia et al. | |
| 2011/0171241 A1 | 7/2011 | Dix et al. | |
| 2012/0020957 A1 | 1/2012 | Lanzavecchia | |
| 2015/0355192 A1 * | 12/2015 | Sun | G16B 20/30 |
| | | | 506/18 |
| 2017/0336404 A1 | 11/2017 | Ali | |
| 2018/0179519 A1 | 6/2018 | Wang et al. | |
| 2020/0135299 A1 * | 4/2020 | Wang | G16B 35/10 |

FOREIGN PATENT DOCUMENTS

| | | |
|---|---|---|
| CN | 105954512 A | 9/2016 |
| EP | 0239400 B1 | 8/1994 |
| GB | 2188638 A | 10/1987 |
| WO | 2005/087812 A1 | 9/2005 |

(Continued)

OTHER PUBLICATIONS

Winter et al., Man-made antibodies, Nature, 349:293-299 (1991).
Woodlock et al., Active specific immunotherapy for metastatic colorectal carcinoma: phase I study of an allogeneic cell vaccine plus low-dose interleukin-1 alpha, J. Immunother., 22:251-259 (1999).
Xu et al., Epitope-based vaccine design yields fusion peptide-directed antibodies that neutralize diverse strains of HIV-1, Nature Medicine, 24(6):857-867 (2018).
Yu et al., Beyond Antibodies as Binding Partners: The Role of Antibody Mimetics in Bioanalysis, Annual Review of Analytical Chemistry, 10:293-320 (2017).
Yuan et al., Using PyMOL as a platform for computational drug design, Computational Molecular Science, 7:e1298 (2017).

(Continued)

Primary Examiner — Anna Skibinsky
(74) Attorney, Agent, or Firm — MARSHALL, GERSTEIN & BORUN LLP

(57) ABSTRACT

Provided herein are methods implemented by a processor in a computer for designing a clamp peptide comprising the structure $A_1$-B-$A_2$ wherein $A_1$ is a first peptide arm that binds to a first binding site of a target protein, $A_2$ is a second peptide arm that binds to a second binding site of the target protein, and B is a bridge peptide which links $A_1$ to $A_2$. Also provided herein are computer-readable storage media having stored thereon machine-readable instructions executable by a processor and systems. Related methods of manufacturing a clamp peptide and the clamp peptides manufactures by the methods are provided.

14 Claims, 7 Drawing Sheets

Specification includes a Sequence Listing.

(56) References Cited

FOREIGN PATENT DOCUMENTS

| WO | 2010/051007 A1 | 5/2010 |
|---|---|---|
| WO | 2016/022071 A1 | 2/2016 |
| WO | 2016/069245 A1 | 5/2016 |
| WO | 2017/197477 A1 | 11/2017 |

OTHER PUBLICATIONS

Zhao et al., Structural Basis of Zika Virus-Specific Antibody Protection, Cell, 166:1016-1027 (2016).
Krammer et al., LigScore: a novel scoring function for predicting binding affinities, J. Molecular Graphics and Modelling, 23(5):395-407 (2005).
Li et al., Electrochemical aptamer-based sensors for food and water analysis: A review, Analytica. Chimica. Acta., (2018).
Lin et al., Selective dispersive solid phase extraction-chromatography tandem mass spectrometry based on aptamer-functionalized UiO-66-NH2 for determination of polychlorinated biphenyls, Journal of Chromatography A, 1446:34-40 (2016).
Logean et al., Customized versus universal scoring functions: application to class I MHC-peptide binding free energy predictions, Bioorganic and Medicinal Chem Lett., 11(5):675-679 (2001).
Loos et al., Current Zika virus epidemiology and recent epidemics, Medicine ET Maladies Infectieuses, 44(7):302-307 (2014).
Macalino et al., Role of computer-aided drug design in modern drug discovery, Archives of Pharmacal. Research, 38(9):1686-1701 (2015).
Magnani et al., A human inferred germline antibody binds to an immunodominant epitope and neutralizes Zika virus, PLoS Negl. Trop. Dis., 11:39-42:1-17, e0005655 (2017).
Magnani et al., Neutralizing human monoclonal antibodies prevent Zika virus infection in macaques, Science Translational Medicine, 9(410):eaan8184 (2017).
Marvin et al., Recombinant approaches to IgG-like bispecific antibodies, Acta. Pharmacologica. Sinica., 26:649-658 (2005).
Mascini et al., Hairpin DNA-AuNPs as molecular binding elements for the detection of volatile organic compounds, Biosensors and Bioelectronics, 123:124-130 (2019).
Mascini et al., Selective solid phase extraction of JWH synthetic cannabinoids by using computationally designed peptides, Talanta, 167:126-133 (2017).
McEnaney et al., Chemically Synthesized Molecules with the Targeting and Effector Functions of Antibodies, J. Am. Chem. Soc., 136(52):18034-18043 (2014).
Michaeli et al., Computationally Designed Bispecific MD2/CD14 Binding Peptides Show TLR4 Agonist Activity, The Journal of Immunology, 201(11):3383-3391 (2018).
Morrison et al., Chimeric human antibody molecules: mouse antigen-binding domains with human constant region domains, Proc. Natl. Acad. Sci., 81:6851-6855 (1984).
Neuberger et al., Recombinant antibodies possessing novel effector functions, Nature, 312:604-608 (1984).
O'Hara et al., Ligand binding assays in the 21st century laboratory: recommendations for characterization and supply of critical reagents, AAPS J., 14(2):316-328 (2012).
OE Docking. version 3.0.0. Open Eye Scientific Software, Santa Fe, NM. http://www.eyesopen.com.
Omega. version 2.4.6. OpenEye Scientific Software, Santa Fe, NM. http://www.eyesopen.com.
Orlandi et al., Cloning immunoglobulin variable domains for expression by the polymerase chain reaction, Proc. Natl. Acad. Sci., 86:3833-3837 (1989).
Pawley et al., Highly Sensitive and Selective Direct Detection of Zika Virus Particles in Human Bodily Fluids for Accurate Early Diagnosis of Infection, ACS Omega, 4(4):6808-6818 (2019).
Pedersen et al., Comparison of Surface Accessible Residues in Human and Murine Immunoglobulin Fv Domains: Implication for Humanization of Murine Antibodies, Journal of Molecular Biology, 235:959-973 (1994).
Perez et al., Peptides trapping dioxins: a docking-based inverse screening approach, Journal of Chemistry, 2013.
Pichon et al., Aptamer-based-sorbents for sample treatment—a review, Anal. Bioanal. Chem., 407(3):681-698 (2015).
Priyamvada et al., Human antibody responses after dengue virus infection are highly cross-reactive to Zika virus, Proceedings of the National Academy of Sciences, 113(28):7852-7857 (2016).
Rajkovic et al., Immunoquantitative real-time PCR for detection and quantification of *Staphylococcus aureus* enterotoxin Bin foods, Applied and Environmental Microbiology, 72(10):6593-6599 (2006).
Raveh et al., Rosetta FlexPepDock ab-initio: simultaneous folding, docking and refinement of peptides onto their receptors, PLoS One, 6(4):e18934 (2011).
Reiter et al., Engineering interchain disulfide bonds into conserved framework regions of Fv fragments: improved biochemical characteristics of recombinant immunotoxins containing disulfide-stabilized Fv, Protein Engineering, 7:697-704 (1994).
Roder et al., The EBV-hybridoma technique, Methods in Enzymology, 121:140-167 (1986).
Roque et al., Antibodies and genetically engineered related molecules: production and purification, Biotechnology Progressg., 20(3):639-54 (2004).
Routledge et al., The effect of aglycosylation on the immunogenicity of a humanized therapeutic CD3 monoclonal antibody, Transplantation, 60:847-853, (1995).
Sankaranarayanan et al., Broadly Neutralizing Antibodies for therapy of viral Infections, Antibody Tech. Journal, 6:1-15 (2016).
Shields et al., High resolution mapping of the binding site on human IgG1 for Fc gamma RI, Fc gamma RII, Fc gamma RIII, and FcRn and design of IgG1 variants with improved binding to the Fc gamma R, J. Biol. Chem., 276:6591-6604 (2001).
Shukla et al., Rapid Detection Strategies for the Global Threat of Zika Virus: Current State, New Hypotheses, and Limitations, Frontiers in Microbiology, Oct. 24, 2014 (Oct. 24, 2016), vol. 7, Art. 1685, pp. 1-15.
Singh et al., Rational Design of Small Peptides for Optimal Inhibition of Cyclooxygenase-2: Development of a Highly Effective Anti-Inflammatory Agent, Journal of Medicinal Chemistry, 59(8):3920-3934 (2016).
Sirohi et al., The 3.8 A resolution cryo-EM structure of Zika virus, Science, 352(6284):467-470 (2016).
Stettler et al., Specificity, cross-reactivity, and function of antibodies elicited by Zika virus infection, Science, 353(6301):823-826 (2016).
Stobiecka et al., Biosensors based on molecular beacons, Chemical Papers, 69:62-76 (2015).
Szybki. version 1.5.2. OpenEye Scientific Software, Santa Fe, NM. http://www.eyesogen.com.
Takahashi et al., Induction of CD8+ cytotoxic T cells by immunization with purified HIV-1 envelope protein in ISCOMs, Nature, 344:873-875 (1990).
Takeda et al., Construction of chimaeric processed immunoglobulin genes containing mouse variable and human constant region sequences, Nature, 314:452-454 (1985).
Tambunan et al., Designing disulfide cyclic peptide as fusion inhibitor that targets denv envelope proteine, Jurnal Teknologi, 78:4-3 (2016).
Tang et al., Quantum dot-DNA aptamer conjugates coupled with capillary electrophoresis: A universal strategy for ratiometric detection of organophosphorus pesticides, Talanta, 146:55-61 (2016).
Titus et al., Human T cells targeted with anti-T3 cross-linked to antitumor antibody prevent tumor growth in nude mice, J. Immunol., 138:4018-4022 (1987).
Todorovska et al., Design and application of diabodies, triabodies and tetrabodies for cancer targeting, Journal of Immunological Methods, 248:47-66, (2001).
Tomasevic et al., A high affinity recombinant antibody to the human EphA3 receptor with enhanced ADCC activity, Growth Factors, 32:223-235 (2014).
Trott et al., AutoDock Vina: Improving the speed and accuracy of docking with a new scoring function, efficient optimization, and multithreading, J. Computational Chem., 31(2):455-461 (2010).

(56) References Cited

OTHER PUBLICATIONS

Tsekenis et al., Label-less immunosensor assay for myelin basic protein based upon an ac impedance protocol, Analytical Chemistry, 80(6):2058-2062 (2008).
Vida. version 4.1.1. OpenEye Scientific Software, Santa Fe, NM. http://www.eyesogen.com.
Warren et al., Future prospects for vaccine adjuvants, CRC Critical Reviews in Immunology, 8:83-101 (1988).
Weaver et al., Zika virus: History, emergence, biology, and prospects for control, Antiviral Research, 130:69-80 (2016).
Acebes et al., Rational enzyme engineering through biophysical and biochemical modeling, ACS Catalysis, 6(3), 1624-1629 (2016).
Armour et al., Recombinant human IgG molecules lacking Fcgamma receptor I binding and monocyte triggering activities, Eur. J. Immunol., 29:2613-2624, (1999).
Barba-Spaeth et al., Structural basis of potent Zika-dengue virus antibody cross-neutralization, Nature, 536(7614):48-53 (2016).
Binz and Pluckthun, Engineered proteins as specific binding reagents, Curr Opin Biotechnol., 16(4):459-69 (2005).
Bohm et al., Combinatorial docking and combinatorial chemistry: design of potent non-peptide thrombin inhibitors, J. Computer-Aided Molecular Design, 13(1):51-56 (1999).
Bunker et al., Rational Design of Liposomal Drug Delivery Systems, a Review: Combined Experimental and Computational Studies of Lipid Membranes, Liposomes and Their PEGylation, Biochimica et Biophysica Acta (BBA)-Biomembranes, 1858(10):2334-2352 (2016).
Burch et al., Priming Tissue-specific Cellular Immunity in a Phase I Trial of Autologous Dendritic Cells for Prostate Cancer, Clinical Cancer Research, 6(6):2175-2182 (2000).
Burmeister et al., Crystal structure of the complex of rat neonatal Fc receptor with Fc, Nature, 372:379-383, (1994).
Byrne et al., A tale of two specificities: bispecific antibodies for therapeutic and diagnostic applications, Trends Biotechnol., 31:621-632 (2013).
Campos et al., Prolonged detection of Zika virus RNA in urine samples during the ongoing Zika virus epidemic in Brazil, Journal of Clinical Virology, 77:69-70 (2016).
Chan et al., Therapeutic antibodies for autoimmunity and inflammation, Nat Rev Immunol., 10:301-316 (2010).
Cole et al., Monoclonal Antibodies and Cancer Therapy, Alan R Liss Inc, New York N.Y., 77-96 (1985).
Cote et al., Generation of human monoclonal antibodies reactive with cellular antigens, Proc Natl Acad Sci., 80:2026-2030 (1983).
Cross et al., Analytical Validation of the ReEBOV Antigen Rapid Test for Point-of-Care Diagnosis of Ebola Virus Infection, The Journal of Infectious Diseases, 214(suppl3):S210-S217 (2016).
Cuesta et al., Multivalent antibodies: when design surpasses evolution, Trends in Biotechnology, 28:355-362 (2010).
Dai et al., Structures of the Zika Virus Envelope Protein and Its Complex with a Flavivirus Broadly Protective Antibody, Cell Host & Microbe., 19(5):696-704 (2016).
Davis et al., Single Chain Antibody (SCA) Encoding Genes: One-Step Construction and Expression in Eukaryotic Cells, Nature Biotechnology, 9:165-169 (1991).
Dudley et al., Adoptive cell therapy for patients with metastatic melanoma: evaluation of intensive myeloablative chemoradiation preparative regimens, J. Clin. Oneal., 26:5233-5239 (2008).
Friend et al., Phase I study of an engineered aglycosylated humanized CD3 antibody in renal transplant rejection, Transplantation, 68:1632-1637 (1999).
Gofflot et al., Immuno-quantitative polymerase chain reaction for detection and quantitation of prion protein, Journal of Immunoassay and Immunochemistry, 25(3):241-258 (2004).
Gold et al., Aptamers As Therapeutic And Diagnostic Agents, J. Biotechnol., 74:5-13 (2000).
Gong et al., Peptide Aptamer: a powerful potential tool in plant functional genomics (English Abstract only), Hereditas., 32(6):548-554 (2010).
Gonzalez-Diaz et al., Plasmonic Au/Co/Au nanosandwiches with Enhanced Magneto-Optical Activity, Small, 4(2):202-205 (2008).
Grant et al., A paper-based immunoassay to determine HPV vaccination status at the point-of-care, Vaccine, 34(46):5656-5663 (2016).
Gridelli et al., Efficient Human Fetal Liver Cell Isolation Protocol Based on Vascular Perfusion for Liver Cell-Based Therapy and Case Report on Cell Transplantation, Liver Transplantation, 18:226-237 (2012).
Haskard and Archer, The production of human monoclonal autoantibodies from patients with rheumatoid arthritis by the EBV-hybridoma technique, Journal of Immunological Methods, 74(2):361-367 (1984).
Hawkins et al., Conformer Generation with Omega: Algorithm and Validation Using High Quality Structures from the Protein Databank and Cambridge Structural Database, Journal of Chemical Information and Modeling, 50(4):572-584 (2010).
Hawkins et al., Conformer Generation with Omega: Learning from the Data Set and the Analysis of Failures, Journal of Chemical Information and Modeling, 52(11):2919-2936, (2012).
Heffron et al., Antibody responses to Zika virus proteins in pregnant and non-pregnant macaques, PLoS Neglected Tropical Diseases, 12(11):e0006903 (2018).
Holliger et al., Engineered antibody fragments and the rise of single domains, Nat. Biotechnol., 23:1126-1136 (2005).
Hoover et al., Adjuvant active specific immunotherapy for human colorectal cancer: 6.5-year median follow-up of a phase III prospectively randomized trial, J Clin Oncol., 11:390-399 (1993).
Hu et al., Minibody: A Novel Engineered Anti-Carcinoembryonic Antigen Antibody Fragment (Single-Chain Fv-CH3) Which Exhibits Rapid, High-Level Targeting of Xenografts, Cancer Research, 56:3055-3061 (1996).
Huse et al., Generation of a large combinatorial library of the immunoglobulin repertoire in phage lambda, Science, 246:1275-1281 (1989).
Huzly et al., High specificity of a novel Zika virus ELISA in European patients after exposure to different flaviviruses, Euro. Surveillance, 21:1-4 (2016).
Hwang et al., High sensitive and selective electrochemical biosensor: Label-free detection of human norovirus using affinity peptide as molecular binder, Biosensors and Bioelectronics, 87:164-170 (2017).
International Preliminary Report on Patentability for Corresponding International Application No. PCT/US2017/059128, dated May 9, 2019.
International Preliminary Report on Patentability for Corresponding International Application No. PCT/US2017/059129, dated May 9, 2019.
International Search Report and Written Opinion for Corresponding International Application No. PCT/US2017/059128, dated Feb. 16, 2018.
International Search Report and Written Opinion for Corresponding International Application No. PCT/US2017/059129, dated Jan. 18, 2018.
International Search Report and Written Opinion for corresponding International Application No. PCT/US2019/061862, dated Feb. 14, 2020.
Karpovsky et al., Production of target-specific effector cells using hetero-cross-linked aggregates containing anti-target cell and anti-Fc gamma receptor antibodies, J. Exp. Med., 160:1686-701 (1984).
Kelley et al., POSIT: flexible shape-guided docking for pose prediction, Journal of Chemical Information and Modeling, 55(8):1771-1780 (2015).
Khan et al., Human fetal liver-derived stem cell transplantation as supportive modality in the management of end-stage decompensated liver cirrhosis, Cell Transplant, 19:409-418 (2010).
Kim et al., Development of a novel peptide aptamer-based immunoassay to detect Zika virus in serum and urine, Theranostics, 8(13):3629-3642 (2018).
Koehler et al., Continuous cultures of fused cells secreting antibody of predefined specificity, Nature, 256:495-497, (1975).
Kortt et al., Dimeric and trimeric antibodies: high avidity scFvs for cancer targeting, Biomolecular Engineering, 18:95-108, (2001).

(56) References Cited

OTHER PUBLICATIONS

Kozbor et al., The production of monoclonal antibodies from human lymphocytes, Immunol. Today, 4:72-79 (1983).

* cited by examiner

METHODS OF DESIGNING NOVEL ANTIBODY MIMETICS FOR USE IN DETECTING ANTIGENS AND AS THERAPEUTIC AGENTS

CROSS-REFERENCE TO RELATED APPLICATION(S)

This application claims priority to U.S. Provisional Application No. 62/684,960, filed on Jun. 14, 2018, the contents of which are incorporated herein by reference.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: 68,786 byte ASCII (Text) file named "53192A_Seqlisting.txt"; created on Jun. 12, 2019.

BACKGROUND

Antibodies constitute powerful therapeutic agents characterized by limited side effects due to their ability to specifically target a distinct antigen on a cell, bacteria, virus, or toxin. In 1986, the first therapeutic monoclonal antibody, Orthoclone OKT3, was introduced into the market. Since then, this class of biopharmaceutical products has significantly grown and over 45 monoclonal antibody products had received approval in the U.S. or Europe for the treatment of a variety of diseases, including cancer and inflammatory, cardiovascular, respiratory, and infectious diseases. Though the projected antibody market in the United States is anticipated to surpass the $10 billion mark, the production of such therapeutics is not without limitations. One disadvantage of therapeutic antibodies is the cost of downstream processing to achieve the required high purity levels. Another limiting factor of therapeutic antibodies is the sensitivity of antibody structure to chemical and physical denaturation encountered during post-manufacture filling, shipping and storage. Harsh chemical environments can affect the antibodies' binding properties.

Antibody mimetics have been successfully used in the development of binding assays for the detection of analytes in biological samples, as well as in separation methods, cancer therapy, targeted drug delivery, and in vivo imaging. The recent advances in the field of antibody mimetics and their applications in bioanalytical chemistry, specifically in diagnostics and other analytical methods have been described (Yu et al., *Annual Review of Analytical Chemistry* 10, 293-320 (2017). Because synthetic peptides are more resistant to physicochemical stress, characteristically more reproducible, and, ultimately, less expensive to manufacture and commercialize, when compared to antibodies, their use as elements of antibody mimetics capable of binding to ligand analytes in a manner analogous to that of the antigen-antibody interaction has spurred increased interest in the biotechnology and bioanalytical communities. To produce antibody mimetics that outperform antibodies with regard to binding affinities, cellular and tumor penetration, large-scale production, and temperature and pH stability is a high priority goal of the industry (Yu et al., 2017, supra).

In recent works, short peptides were used as molecular binders for virus detection. Linear peptides were selected by phage display to detect norovirus using an ELISA protocol or by means of an impedance biosensor (Hwang et al., 2017; Palzkill et al., 2018). Computationally-designed peptides were used to possibly detect flavivirus. The binding affinity and stability of disulfide cyclic peptide ligands with target Dengue virus (DENV) E glycoprotein were calculated by molecular docking and molecular dynamics simulation, but no experimental evidence was provided (Tambunan et al., 2016). A recent report predicted by molecular docking the structure of short peptides targeting the Zika virus (ZIKV) envelope protein and the interactions between the selected peptides and virus were assessed via a fluorescence-linked sandwich immunosorbent assay (FLISA), and the performance of the peptide-linked sandwich FLISA was evaluated in virus-spiked human serum and urine (Do Thi Hoang Kim et al., 2018).

While in silico methods of molecular modeling has been used to minimize experimental problems and facilitate the rational design of experimental protocols (Acebes et al., 2016; Bunker et al., 2016; Singh et al., 2016; Michaeli et al., 2018; Xu et al., 2018), and even though virtual docking is currently an important tool in drug discovery, and a subject of important developments over the last decade (Macalino et al., 2015; Yuan et al., 2017), a number of obstacles still limits the widespread use of molecular modeling for biotechnological applications. One of the most important drawbacks for mainstream use of molecular modeling is the challenge to simulate a huge number of candidates to be designed or/and docked using a full combinatorial approach.

Thus, improved methods of designing peptides for use in antibody mimetics is needed.

SUMMARY

Presented herein for the first time is a new methodology, based on an incremental construction approach, for the design and selection of short peptides that function as binding agents capable of selectively detecting target molecules. Herein, an in silico semi-combinatorial peptide screening method for designing the target-binding portions, the arms, of a new class of antibody mimetics, called clamp peptides, is demonstrated. In this virtual peptide screening method, different docking cycles of peptide libraries were generated and evaluated for binding to a binding site of a target protein. Using this method, the recognition properties of the amino acid motif between target binding and non-specific binding were maximized and allowed for ~3 million peptides to be tested in a short period of time. Using this virtual screening method, clamp peptides designed to bind to two different binding sites on the ZIKV envelope protein were designed and subsequently manufactured and tested. As shown through direct ELISA, the performances of the clamp peptides demonstrated beneficial and desired binding activities. As shown by the data presented herein, the arms of the clamp peptides were able to wrap around the glycosylation site such as to clamp the peptide in place.

The present disclosure provides a method implemented by a processor in a computer for designing a clamp peptide comprising the structure $A_1$-B-$A_2$ wherein $A_1$ is a first peptide arm that binds to a first binding site of a target protein, $A_2$ is a second peptide arm that binds to a second binding site of the target protein, and B is a bridge peptide which links $A_1$ to $A_2$. In exemplary embodiments, the method comprises the steps of: (a) determining a binding score of each tetrapeptide of a first peptide library for the first binding site of the target protein, wherein the first peptide library comprises a set of tetrapeptides having a unique combination of four amino acids of the twenty naturally-occurring amino acids, optionally, wherein the first peptide library comprises the full combinatorial set of 160,000 tetrapeptides having a unique combination of four amino acids of the twenty naturally-occurring amino acids, (b) identifying the sequences of the tetrapeptides having a binding score which meets a first threshold, (c) determining a binding score of each pentapeptide of a second peptide library for the first binding site of the target protein, wherein the second peptide library comprises a set of pentapeptides having a unique combination of five amino acids comprising the amino acids of the sequence of a tetrapeptide identified in step (b) and one of the twenty naturally-occurring amino acids added as the first amino acid or the fifth amino acid of the pentapeptide or between two amino acids of the sequence of the tetrapeptide, and (d) identifying the sequences of the pentapeptides having a binding score which meets a second threshold. In exemplary embodiments, the method further comprises the steps of: (e) determining a binding score of each hexapeptide of a third peptide library for the first binding site of the target protein, wherein the third peptide library comprises a set of hexapeptides having a unique combination of six amino acids comprising the amino acids of the sequence of a pentapeptide identified in step (d) and one of the twenty naturally-occurring amino acids added as the first amino acid or the sixth amino acid of the hexapeptide or between two amino acids of the sequence of the pentapeptide and (f) identifying the sequences of the hexapeptides having a binding score which meets a third threshold. In exemplary embodiments, the method further comprises the steps of: repeating at least steps (a) to (d) wherein, for each determining step, a binding score for the second binding site of the target protein is determined for each tetrapeptide of the first peptide library and for each pentapeptide of the second peptide library. Optionally, wherein, when the method further comprises determining a binding score of each hexapeptide of a third peptide library for the first binding site of the target protein, the method further comprises repeating these steps, wherein for each determining step, a binding score for the second binding site of the target protein is determined for each hexapeptide of the third peptide library.

The present disclosure also provides a computer-readable storage medium having stored thereon machine-readable instructions executable by a processor, comprising instructions for carrying out the steps of any one of the presently disclosed methods for designing a clamp peptide.

Further provided is a system comprising machine readable instructions that, when executed by the processor, cause the processor to carry out the steps of any one of the presently disclosed methods for designing a clamp peptide.

The present disclosure also provides a method of manufacturing a clamp peptide comprising the structure $A_1$-B-$A_2$ wherein $A_1$ is a first peptide arm that binds to a first binding site of a target protein, $A_2$ is a second peptide arm that binds to a second binding site of the target protein, and B is a bridge peptide which links $A_1$ to $A_2$. In exemplary embodiments, the method comprises (i) designing the first peptide arm and the second peptide arm of the clamp peptide according to any one of the presently disclosed methods for designing a clamp peptide and (ii) joining the first peptide arm to the second peptide arm with a bridge peptide, B.

A clamp peptide comprising the structure $A_1$-B-$A_2$ wherein $A_1$ is a first peptide arm that binds to a first binding site of a target protein, $A_2$ is a second peptide arm that binds to a second binding site of the target protein, and B is a bridge peptide which links $A_1$ to $A_2$, wherein the sequences of $A_1$ and $A_2$ are designed by any one of the presently disclosed methods for designing a clamp peptide.

Use of the presently disclosed clamp peptides for detecting target proteins, e.g., antigens, are furthermore provided herein. Also, use of the presently disclosed clamp peptides for treating a subject in need thereof are provided herein.

Additional descriptions and guidance, as well as exemplification, of the presently disclosed methods are provided herein.

DETAILED DESCRIPTION

Figure 1B:
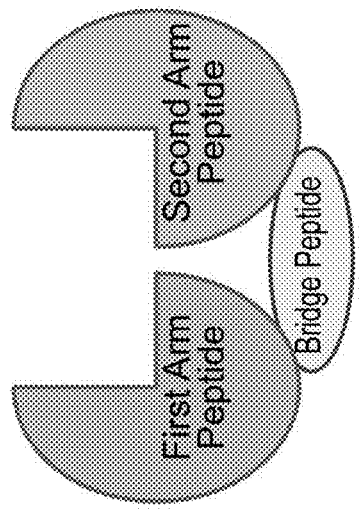
FIG. 1B is a schematic representation of the clamp peptide structure made by two peptide arms of five or six amino acids in length linked by a bridge peptide.

The present disclosure provides a method implemented by a processor in a computer for designing a clamp peptide. Clamp peptides, as further described herein, represent a new class of antibody mimetics. In exemplary aspects, the clamp peptide comprises the structure $A_1$-B-$A_2$ wherein $A_1$ is a first peptide arm that binds to a first binding site of a target protein, $A_2$ is a second peptide arm that binds to a second binding site of the target protein, and B is a bridge peptide which links $A_1$ to $A_2$. In exemplary aspects, each of $A_1$ and $A_2$ is a peptide of about 5 to about 7 amino acids, e.g., about 5 amino acids, about 6 amino acids, or about 7 amino acids. In exemplary aspects, the bridge peptide (B) is about 5 to about 10 amino acids in length (e.g., about 5 amino acids, about 6 amino acids, about 7 amino acids, about 8 amino acids, about 9 amino acids, or about 10 amino acids in length. In various aspects, the amino acids of the clamp peptide, or the first peptide arm, the second peptide arm, or the bridge peptide thereof, are naturally-occurring or coded or non-naturally occurring or non-coded. Non-naturally occurring amino acids refer to amino acids that do not naturally occur in vivo but which, nevertheless, can be incorporated into the peptide structures described herein. "Non-coded" as used herein refer to an amino acid that is not an L-isomer of any of the following 20 amino acids: Ala, Cys, Asp, Glu, Phe, Gly, His, Ile, Lys, Leu, Met, Asn, Pro, Gln, Arg, Ser, Thr, Val, Trp, Tyr. Naturally-occurring or coded amino acids include the L-isomers of the amino acids: Ala, Cys, Asp, Glu, Phe, Gly, His, Ile, Lys, Leu, Met, Asn, Pro, Gln, Arg, Ser, Thr, Val, Trp, Tyr. Exemplary non-naturally occurring or non-coded amino acids include but are not limited to, any D or L isomers of the non-naturally occurring or non-coded amino acids selected from the group consisting of: beta-alanine, N-alpha-methyl-alanine (Me-Ala), aminobutyric acid (Abu), gamma-aminobutyric acid, aminohexanoic acid (epsilon-Ahx), aminoisobutyric acid (Aib), aminomethylpyrrole carboxylic acid, aminopiperidinecarboxylic acid, aminoserine (Ams), am inotetrahydropyran-4-carboxylic acid, arginine N-methoxy-N-methyl amide, beta-aspartic acid (beta-Asp), azetidine carboxylic acid, 3-(2-benzothiazolyl)alanine, alpha-tert-butylglycine, 2-amino-5-ureido-n-valeric acid (citrulline, Cit), beta-Cyclohexylalanine (Cha), acetamidomethyl-cysteine, diaminobutanoic acid (Dab), diaminopropionic acid (Dpr), dihydroxyphenylalanine (DOPA), dimethylthiazolidine (DMTA), gamma-Glutamic acid (gamma-Glu), homoserine (Hse), hydroxyproline (Hyp), isoleucine N-methoxy-N-methyl amide, methyl-isoleucine (MeIle), isonipecotic acid (Isn), methyl-leucine (MeLeu), methyl-lysine, dimethyl-lysine, trimethyl-lysine, methanoproline, methionine-sulfoxide (Met(O)), methionine-sulfone (Met($O_2$)), norleucine (Nle), methyl-norleucine (Me-Nle), norvaline (Nva), ornithine (Orn), para-aminobenzoic acid (PABA), penicillamine (Pen), methylphenylalanine (MePhe), 4-Chlorophenylalanine (Phe(4-Cl)), 4-fluorophenylalanine (Phe(4-F)), 4-nitrophenylalanine (Phe(4-$NO_2$)), 4-cyanophenylalanine ((Phe(4-CN)), phenylglycine (Phg), piperidinylalanine, piperidinylglycine, 3,4-dehydroproline, pyrrolidinylalanine, sarcosine (Sar), selenocysteine (Sec), O-Benzyl-phosphoserine, 4-amino-3-hydroxy-6-methylheptanoic acid (Sta), 4-amino-5-cyclohexyl-3-hydroxypentanoic acid (ACHPA), 4-amino-3-hydroxy-5-phenylpentanoic acid (AHPPA), 1,2,3,4,-tetrahydro-isoquinoline-3-carboxylic acid (Tic), tetrahydropyranglycine, thienylalanine (Thi), O-benzyl-phosphotyrosine, O-Phosphotyrosine, methoxytyrosine, ethoxytyrosine, O-(bis-dimethylamino-phosphono)-tyrosine, tyrosine sulfate tetrabutylamine, methyl-valine (Me-Val), and alkylated 3-mercaptopropionic acid. In some embodiments, the clamp peptide, or the first peptide arm, the second peptide arm, or the bridge peptide thereof, described herein are glycosylated, amidated, carboxylated, phosphorylated, esterified, N-acylated, cyclized via, e.g., a disulfide bridge, or converted into a salt (e.g., an acid addition salt, a basic addition salt), and/or optionally dimerized, multimerized, or polymerized, or conjugated.

In exemplary embodiments, the method implemented by a processor in a computer for designing a clamp peptide comprises the steps of: (a) determining a binding score of each tetrapeptide of a first peptide library for the first binding site of the target protein, wherein the first peptide library comprises a set of tetrapeptides having a unique combination of four amino acids of the twenty naturally-occurring amino acids, optionally, wherein the first peptide library comprises the full combinatorial set of 160,000 (160K) tetrapeptides having a unique combination of four amino acids of the twenty naturally-occurring amino acids, (b) identifying the sequences of the tetrapeptides having a binding score which meets a first threshold, (c) determining a binding score of each pentapeptide of a second peptide library for the first binding site of the target protein, wherein the second peptide library comprises a set of pentapeptides having a unique combination of five amino acids comprising the amino acids of the sequence of a tetrapeptide identified in step (b) and one of the twenty naturally-occurring amino acids added as the first amino acid or the fifth amino acid of the pentapeptide or between two amino acids of the sequence of the tetrapeptide, and (d) identifying the sequences of the pentapeptides having a binding score which meets a second threshold.

In exemplary embodiments, the method further comprises the steps of: (e) determining a binding score of each hexapeptide of a third peptide library for the first binding site of the target protein, wherein the third peptide library comprises a set of hexapeptides having a unique combination of six amino acids comprising the amino acids of the sequence of a pentapeptide identified in step (d) and one of the twenty naturally-occurring amino acids added as the first amino acid or the sixth amino acid of the hexapeptide or between two amino acids of the sequence of the pentapeptide and (f) identifying the sequences of the hexapeptides having a binding score which meets a third threshold. In exemplary embodiments, the method further comprises the steps of: repeating at least steps (a) to (d) wherein, for each determining step, a binding score for the second binding site of the target protein is determined for each tetrapeptide of the first peptide library and for each pentapeptide of the second peptide library. Optionally, wherein, when the method further comprises determining a binding score of each hexapeptide of a third peptide library for the first binding site of the target protein, the method further comprises repeating these steps, wherein for each determining step, a binding score for the second binding site of the target protein is determined for each hexapeptide of the third peptide library.

In exemplary embodiments, the method further comprises (I) determining a binding score of each heptapeptide of a fourth peptide library for the first binding site of the target protein, wherein the fourth peptide library comprises a set of heptapeptides having a unique combination of seven amino acids comprising the amino acids of the sequence of a hexapeptide identified in step (f) and one of the twenty naturally-occurring amino acids added as the first amino acid or the seventh amino acid of the hexapeptide or between two amino acids of the sequence of the hexapeptide and (II)

identifying the sequences of the heptapeptides having a binding score which meets a fourth threshold. In exemplary embodiments, the method further comprises the steps of: repeating at least steps of the method, wherein, for each determining step, a binding score for the second binding site of the target protein is determined for each tetrapeptide of the first peptide library and for each pentapeptide of the second peptide library. Optionally, wherein, when the method further comprises determining a binding score of each hexapeptide of a third peptide library and a binding score of each heptapeptide for the first binding site of the target protein, the method further comprises repeating these steps, wherein for each determining step, a binding score for the second binding site of the target protein is determined for each hexapeptide of the third peptide library and for each heptapeptide of the fourth peptide library.

In exemplary embodiments, the method does not further comprise determining a binding score of each heptapeptide of a fourth peptide library. In exemplary instances, the third peptide library is the last peptide library for which binding scores are determined.

The method in some aspects comprises generating the first peptide library. Optionally, the first peptide library comprises 160,000 unique tetrapeptides, optionally, the full combinatorial set of 160,000 tetrapeptides having a unique combination of four amino acids of the twenty naturally-occurring amino acids.

The method in some aspects comprises generating the second peptide library. In various instances, the second peptide library comprises pentapeptides having a sequence based on the sequences of the tetrapeptides (post-application of the first threshold) and another amino acid. In various aspects, the second peptide library comprises a set of pentapeptides having a unique combination of five amino acids comprising the amino acids of the sequence of a tetrapeptide identified in step (b) and one of the twenty naturally-occurring amino acids added as the first amino acid or the fifth amino acid of the pentapeptide or between two amino acids of the sequence of the tetrapeptide.

The method in some aspects comprises generating the third peptide library. In various instances, the third peptide library comprises hexapeptides having a sequence based on the sequences of the pentapeptides (post-application of the second threshold) and another amino acid. In various aspects, the third peptide library comprises a set of hexapeptides having a unique combination of six amino acids comprising the amino acids of the sequence of a pentapeptide identified in step (d) and one of the twenty naturally-occurring amino acids added as the first amino acid or the sixth amino acid of the hexapeptide or between two amino acids of the sequence of the pentapeptide.

In various instances, the first threshold is a binding score within the top 5% of binding scores (e.g., top binding scores mean the strongest binding between peptide and active site of target protein). In various aspects, approximately 8000 unique sequences of tetrapeptides are identified upon application of the first threshold. In certain aspects, the first threshold is a binding score within the top 5% of binding scores and a binding score outside the top 5% of binding scores for a different target protein. In some instances, about 1000 unique sequences of tetrapeptides are upon application of the first threshold. In exemplary instances, the second threshold is the same as the first threshold. In alternative instances, the first threshold is different from the second threshold. In exemplary instances, the third threshold is the same as the first threshold or the second threshold. In alternative instances, the third threshold is different from the second threshold and/or first threshold. In various aspects, the third threshold is a binding score within the top 5% of binding scores. In certain instances, the third threshold further comprises a binding score outside the top 5% of binding scores for a different target protein.

The binding scores are determined using a molecular docking program, optionally, a molecular docking program that is based on multi-conformer rigid body docking, which evaluates several conformers per peptide. The binding scores in some aspects are calculated using a docking scoring function. In some aspects, one or more of LUDI, Chemscore, chemgauss4, DOCK, FlexX, Gold, Pmf, Score, Fresno, AutoDock Vina, Dynadock, LigScore, Rosetta Flex-PepDock are used for determining and/or calculating the binding score. Such docking scoring functions are known in the art. See, e.g., Logean et al., Bioorganic and Medicinal Chem Lett 11(5): 675-679 (2001), Trott et al., J Computational Chem https://doi.org/10.1002/jcc.21334; Bohm et al., J Computer-Aided Molecular Design 13(1): 51-56 (1999); Raveh et al., PLoS ONE 6(4): e18934. https://doi.org/10.1371/journal.pone.0018934; Krammer et al., J Molecular Graphics and Modelling 23(5): 395-407 (2005). In various instances, the binding scores for more than 350,000 peptides are determined for each of the first binding site and the second binding site.

The method in certain instances further comprises determining the length of B of the clamp peptide, optionally, by measuring the distance between a peptide bound to the first binding site of the target protein and a peptide bound to the second binding site of the target protein. The bridge peptide of the clamp peptide in various aspects is designed based on the length determined.

The present disclosure also provides a computer-readable storage medium having stored thereon machine-readable instructions executable by a processor, comprising instructions for carrying out the steps of any one of the presently disclosed methods for designing a clamp peptide.

Further provided is a system comprising machine readable instructions that, when executed by the processor, cause the processor to carry out the steps of any one of the presently disclosed methods for designing a clamp peptide.

Figure 6A:
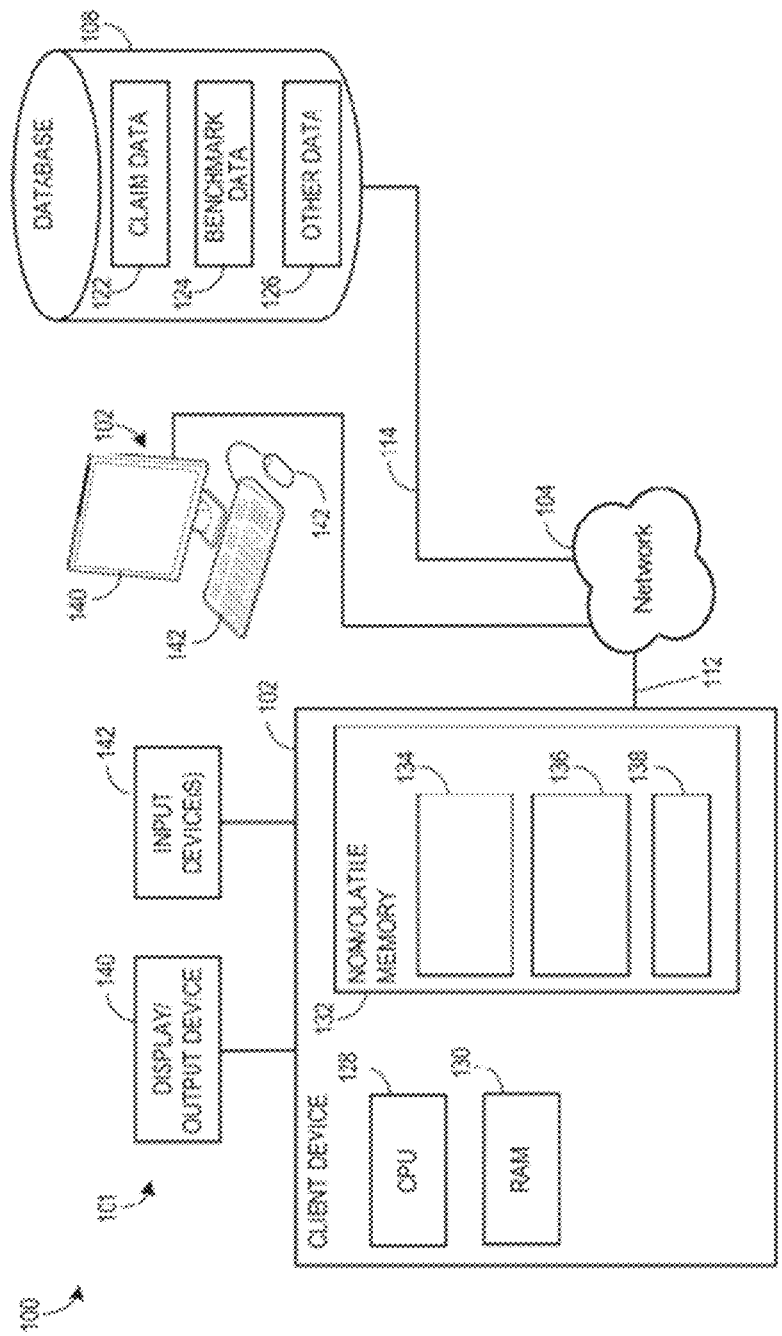
FIG. 6A is a schematic of an exemplary embodiment 101 of a system 100 for designing a clamp peptide.

FIG. 6A illustrates an exemplary embodiment 101 of a system 100 for designing a clamp peptide. Generally, the system 100 may include one or more client devices 102, a network 104, and/or a network-accessible database 108. Each client device 102 may be communicatively coupled to the network 104 by one or more wired or wireless network connections 112, which may be, for example, a connection complying with a standard such as one of the IEEE 802.11 standards ("Wi-Fi"), the Ethernet standard, or any other appropriate network connection. Similarly, the database 108 may be communicatively coupled to the network 104 via one or more connections 114. (Of course, the database could alternatively be internal to one or more of the client devices 102.) The database 108 may store the sequences of each peptide of a peptide library, optionally, the sequences of each tetrapeptide of the first peptide library, the sequences of each pentapeptide of the second peptide library, the sequences of each hexapeptide of the third peptide library. The database 108 additionally or alternatively may store the binding score of each peptide for each peptide library, and/or the identity of the peptide(s) which meet the threshold, and/or the thresholds themselves.

As will be understood, the network 104 may be a local area network (LAN) or a wide-area network (WAN). That is, network 104 may include only local (e.g., intra-organization) connections or, alternatively, the network 104 may include connections extending beyond the organization and onto one or more public networks (e.g., the Internet). In some embodiments, for example, the client device 102 and the database 108 may be within the network operated by a single company (Company A). In other embodiments, for example, the client device(s) 102 may be on a network operated by Company A, while the database 108 may be on a network operated by a second company (Company B), and the networks of Company A and Company B may be coupled by a third network such as, for example, the Internet.

Referring still to FIG. 6A, the client device 102 includes a processor 128 (CPU), a RAM 130, and a non-volatile memory 132. The non-volatile memory 132 may be any appropriate memory device including, by way of example and not limitation, a magnetic disk (e.g., a hard disk drive), a solid state drive (e.g., a flash memory), etc. Additionally, it will be understood that, at least with regard to FIG. 6A, the database 108 need not be separate from the client device 102. Instead, in some embodiments, the database 108 is part of the non-volatile memory 132 and the data 122, 124, 126 may be stored as data within the memory 132. The database may comprise, for instance, the sequences of each tetrapeptide of the first peptide library. The database may further comprise claim data 122 which comprises, for example, the binding scores for each of the tetrapeptides of the first peptide library. Likewise, the database may comprise the sequences of each pentapeptide of the second peptide library and the binding scores for each of the pentapeptides of the second library. Also, the database in some aspects comprises the sequences of each hexapeptide of the third peptide library and the binding scores for each of the hexapeptides of the third library. The benchmark data 124 may comprise binding scores for commercial antibodies to the target protein, which may serve as a benchmark against which the binding scores of the peptides of the peptide libraries may be compared.

Figure 6B:
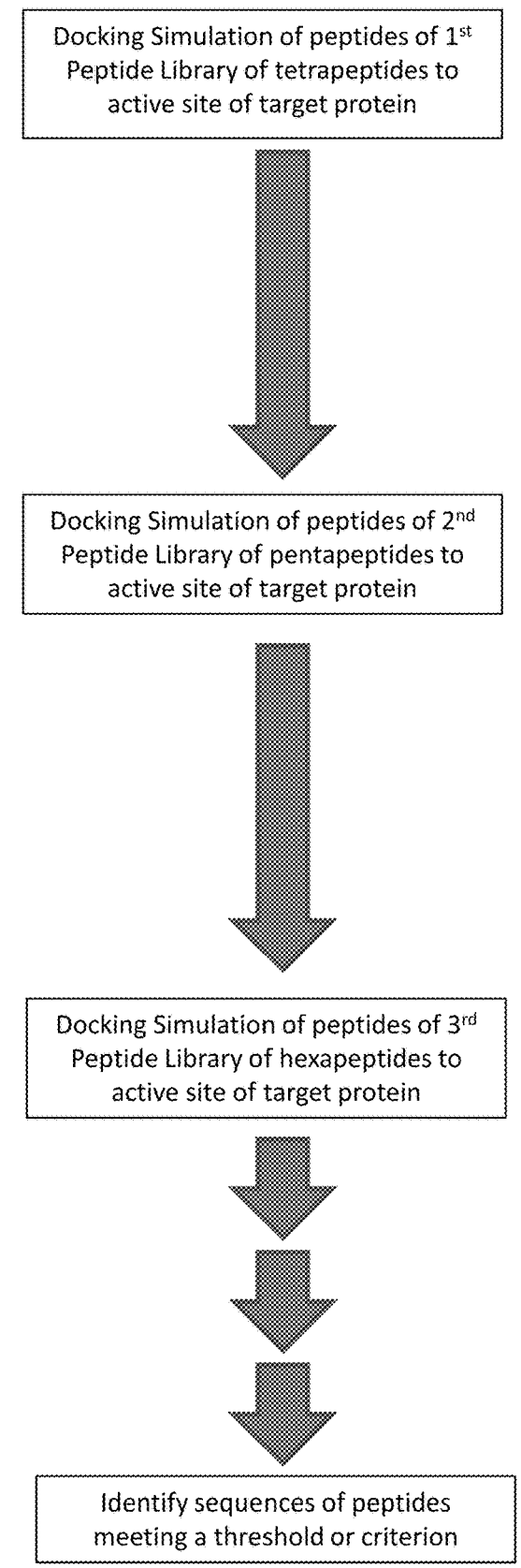
FIG. 6B is a schematic of base routines that may be stored on non-volatile memory of the system 100 of FIG. 6A.
Figure 6C:
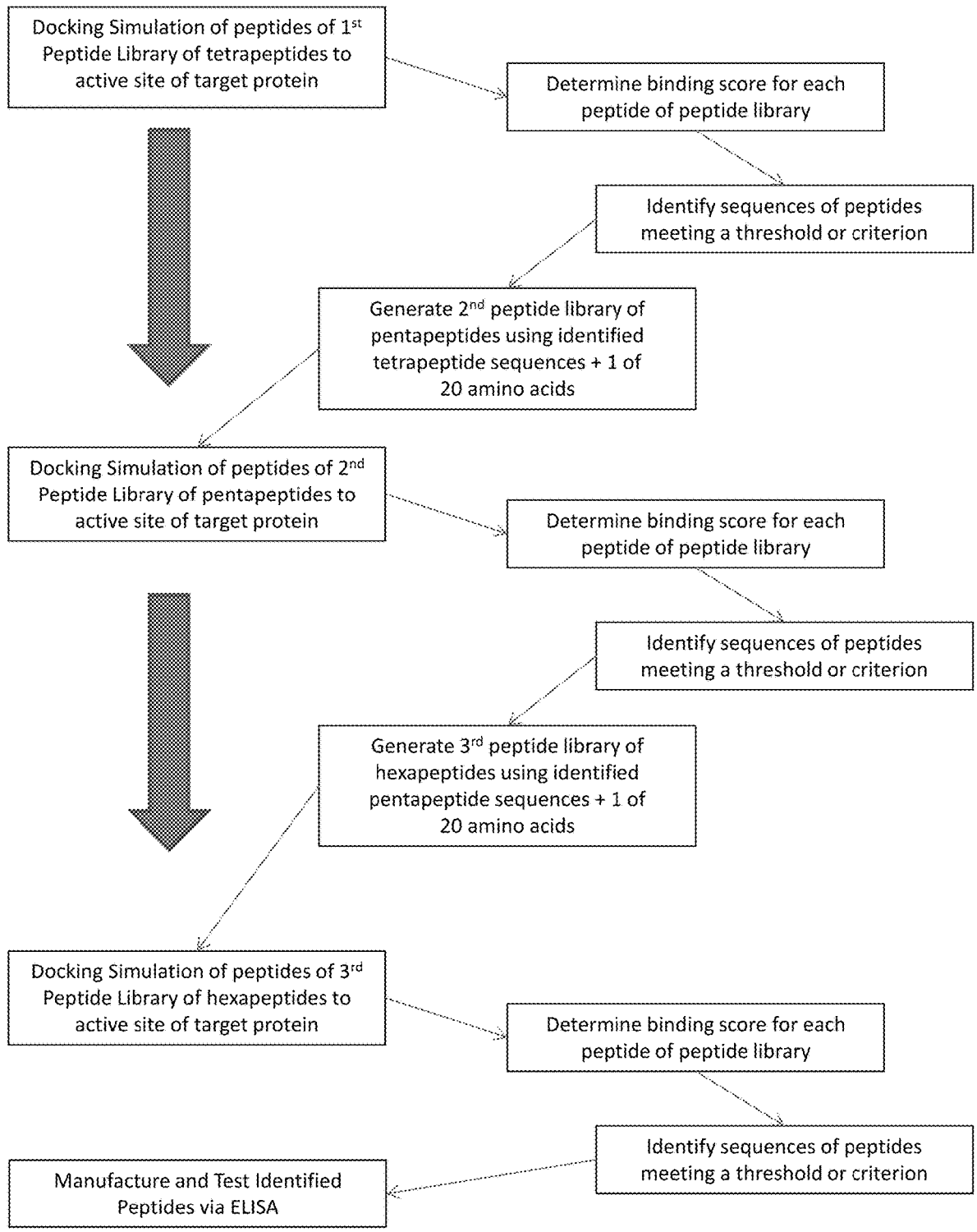
FIG. 6C is a schematic of exemplary sub-routines for the base routines of FIG. 6B.

For example, the data 122 may be included as data in a spreadsheet file stored in the memory 132, instead of as data in the database 108. In addition to storing the records of the database 108 (in some embodiments), the memory 132 stores program data and other data necessary to analyze data (e.g., binding scores) of one or more peptide libraries, determine binding scores, identify the sequences of the peptides which meet a threshold, the thresholds themselves. For example, in an embodiment, the memory 132 stores a first routine 134, a second routine 136, and a third routine 138. The first routine 134 may determine binding scores of each tetrapeptide of a first peptide library for a binding site of the target protein. The second routine 136 may compute one or more statistical parameters of the binding scores collected by the first routine 134, and/or apply a threshold to the binding scores to identify the tetrapeptides (e.g., identify the sequences of the tetrapeptides) meeting that threshold. The third routine 138 may, for example, generate the sequences of pentapeptides of the second peptide library based on the sequences of the tetrapeptides that met the threshold, as identified by the second routine. In exemplary embodiments, the memory 132 stores a first routine 134, a second routine 136, and a third routine 138, as outlined above, and additionally stores a fourth routine, a fifth routine, and a sixth routine. The fourth routine may determine binding scores of each pentapeptide of the second peptide library generated by the third routine for a binding site of the target protein. The fifth routine may compute one or more statistical parameters of the binding scores collected by the fourth routine 134, and/or apply a threshold to the binding scores to identify the pentapeptides (e.g., identify the sequences of the pentapeptides) meeting that threshold. The sixth routine may generate the sequences of hexapeptides of the third peptide library based on the sequences of the pentapeptides that met the threshold, as identified by the fifth routine. The memory 132 may store additional routines for subsequent cycles of determining binding scores of peptides of a peptide library, applying a threshold to identify peptides that meet the threshold, and generating the sequences of the peptides of the next peptide library using the sequences of the peptides meeting the threshold (as identified by the immediately prior routine). For instance, the memory 132 may store a seventh routine, eighth routine, and ninth routine, wherein the seventh routine may determine binding scores of each hexapeptide of a third peptide library for a binding site of the target protein, the eighth routine may compute one or more statistical parameters of the binding scores collected by the seventh routine, and/or apply a threshold to the binding scores to identify the hexapeptides (e.g., identify the sequences of the hexapeptides) meeting that threshold. In exemplary aspects, the memory 132 may store the routines described in FIGS. 6B and 6C.

Regardless, each of the routines is executable by the processor 128 and comprises a series of compiled or compilable machine-readable instructions stored in the memory 132. Additionally, the memory 132 may store generated reports or records of data output by one of the routines 134 or 136. Alternatively, the reports or records may be output to the database 108. One or more display/output devices 140 (e.g., printer, display, etc.) and one or more input devices 142 (e.g., mouse, keyboard, tablet, touch-sensitive interface, etc.) may also be coupled to the client device 102, as is generally known.

As will be understood, although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

For example, the network 104 may include but is not limited to any combination of a LAN, a MAN, a WAN, a mobile, a wired or wireless network, a private network, or a virtual private network. Moreover, while only two clients 102 are illustrated in FIG. 6A to simplify and clarify the description, it is understood that any number of client computers are supported and can be in communication with one or more servers (not shown).

Additionally, certain embodiments are described herein as including logic or a number of routines. Routines may constitute either software routines (e.g., code embodied on a machine-readable medium or in a transmission signal) or hardware routines. A hardware routine is tangible unit capable of performing certain operations and may be configured or arranged in a certain manner. In example embodiments, one or more computer systems (e.g., a standalone, client or server computer system) or one or more hardware routines of a computer system (e.g., a processor or a group of processors) may be configured by software (e.g., an application or application portion) as a hardware routine that operates to perform certain operations as described herein.

Similarly, the methods or routines described herein may be at least partially processor-implemented. For example, at least some of the operations of a method may be performed by one or processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description should be read to include one or at least one and the singular also includes the plural unless it is obvious that it is meant otherwise.

Still further, the figures depict preferred embodiments of a map editor system for purposes of illustration only. One skilled in the art will readily recognize from the following discussion that alternative embodiments of the structures and methods illustrated herein may be employed without departing from the principles described herein Upon reading this disclosure, those of skill in the art will appreciate still additional alternative structural and functional designs for a system and a process for identifying terminal road segments through the disclosed principles herein. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

Methods of manufacturing a clamp peptide are further provided herein. In various aspects, the clamp peptide comprises the structure $A_1$-B-$A_2$ wherein $A_1$ is a first peptide arm that binds to a first binding site of a target protein, $A_2$ is a second peptide arm that binds to a second binding site of the target protein, and B is a bridge peptide which links $A_1$ to $A_2$. In exemplary embodiments, the method comprises (I) designing the first peptide arm and the second peptide arm of the clamp peptide according to any one of the presently disclosed methods implemented by a processor in a computer for designing a clamp peptide and (II) joining the first peptide arm to the second peptide arm with a bridge peptide, B. In exemplary aspects, the method further comprises assaying the binding of the clamp peptide to the target protein. Suitable methods of assaying peptide-protein binding are known in the art and include for instance assays based on Western blotting, an enzyme-linked immunosorbent assay (ELISA), a radioimmunoassay (RIA), and immunohistochemical assay, and ligand binding assays (LBAs) which are described in O'Hara et al., AAPS J 14(2): 316-328 (2012).

The clamp peptides manufactured by any one of the presently disclosed methods of manufacturing a clamp peptide are further provided herein.

The following examples are given merely to illustrate the present invention and not in any way to limit its scope.

EXAMPLES

Example 1

This example describes an exemplary method of designing clamp peptides, a new generation of antibody mimetics.

Abstract

A new class of antibody mimetics is proposed. This is a generic universal approach that can be used against any type of antigen. The antibody mimetics were designed connecting three short peptides mimicking a clamp with two arms and one bridge.

The peptide arms were computationally designed using a virtual approach based on generating different docking cycles of tetra, penta, hexapeptide libraries by maximizing the recognition properties of amino acid motifs between the ZIKV envelope protein active sites and other flaviviruses binding sites (DENV, Chikungunya and West Nile).

The peptide bridge, connecting the two arms, was made with glycine for spacing, proline for bending and two cysteines for biotin functionalization.

Eight clamp peptides and four mono arm peptides were then synthesized and tested vs intact ZIKV particles by using a direct enzyme linked immunosorbent assay (ELISA). As a reference, we employed a well-established anti-ZIKV virus antibody, the antibody 4G2.

Three clamp peptides assay showed a detection limit one or two order of magnitude lower (around $3.16*10^3$ [ZIKV] copies/mL) then the antibody or mono-arm peptides with a dynamic range from $10^4$ to $10^7$ copies/mL of intact ZIKV particles. Synthetic clamp peptides showed low coefficient of variation (<5%) and a good inter-day and batch to batch reproducibility (<15%). These three clamp peptides showed slight cross-reactivity against three serotypes of DENV (DENV-1, -2 and -3) at the concentration of $10^{\wedge}5$ copies/mL of intact virus particles, but the discrimination between the DENV and ZIKV was lost increasing the coating concentration to $10^{\wedge}6$ copies/mL of the viruses.

The sensitivity of the clamp peptides was tested in the presence of two biological matrices, urine and serum diluted 1:1 and 1:10, respectively. The detection limits of clamp peptides decreased about one order of magnitude for ZIKV detection in urine or serum, with a distinct analytical signal starting from $10^{\wedge}5$ copies/mL of ZIKV.

Introduction

The threat of ZIKV infection has emerged as a global public health problem because of its ability to cause severe congenital disease and affect a large population (loos et al., 2014; Weaver et al., 2016). ZIKV infection is known to cause neurological problems to pregnant women and potentially cause microcephaly and other congenital malformations and diseases to the unborn child. ZIKV affects, both male and females and it has been reported that the virus can be transmitted sexually through semen and vaginal fluids. The ZIKV virus is a mosquito-borne flavivirus, and due to the lack of specific antibodies/binders that can be used for diagnosis of the disease, the current bioassays present cross-reactivity with other flaviviruses and arboviruses. It is well established that ZIKV has many common genetic sequences and protein structures with other flaviviruses, like DENV, West Nile virus or Chikungunya (Barba-Spaeth et al., 2016; Heffron et al., 2018). This limits the use of immunoassays for the detection of human pathogens within the flavivirus genus (Priyamvada et al., 2016; Stettler et al., 2016). Thus, there is a need for highly selective binders for ZIKV that can be employed in diagnostics and health status assessment of patients suffering from ZIKV.

The flavivirus envelope protein is responsible for virus entry and represents a major target for neutralizing antibodies. The ZIKV virus structure is similar to other known flaviviruses structures except for the ~10 amino acids that surround the Asn-154 glycosylation site found in each of the 180 envelope glycoproteins that make up the icosahedral shell (Zhao et al., 2016).

In this work, the clamp peptide arms were designed using as guide the crystallographic coordinates of the ZIKV envelope protein glycosylation binding site. The entire molecular surface of the glycosylation envelope protein biding site was defined by two cubic boxes where arm peptides were expected to bind.

The in-silico screening technique was based on a semi-combinatorial approach by designing peptides that could wrap around the glycosylation site such as to clamp the peptide in place. Different docking cycles of peptide libraries were generated by maximizing the recognition properties of the amino acid motif between the ZKV glycosylation site and the other flaviviruses glycosylation binding sites (DENV, Chikungunya and West Nile). A total library of around three million peptides was tested in-silico.

Peptides as antibody mimetic elements in diagnostic methods were recently reviewed highlighting the features desired to outperform antibodies with regard to binding affinities, cellular and tumor penetration, large-scale production, temperature, and pH stability (Yu et al., 2017). It is well documented that a hard chemical environment can affect antibodies binding properties and DNA and peptides aptamers are the most promising candidates to replace them in bioanalysis as reported by recent reviews (Gong et al., 2010; Pichon et al., 2015; Li et al., 2018). Aptamers have become increasingly important molecular tools for diagnostics and as therapeutic agents, and are used in many analytical applications, such as chromatography, electrophoresis, mass spectrometry, molecular beacons, gas sensors, and biosensors (Stobiecka and Chalupa, 2015; Lin et al., 2016; Tang et al., 2016; Mascini et al., 2017; Mascini et al., 2019).

In recent works, short peptides were used as molecular binders for virus detection. Linear peptides were selected by phage display to detect norovirus using an ELISA protocol or by means of an impedance biosensor (Hwang et al., 2017; Palzkill et al., 2018).

Computationally designed peptides were used to possibly detect flavivirus. Binding affinity and stability of disulfide cyclic peptide ligands with target DENV E glycoprotein were calculated by molecular docking and molecular dynamics simulation, but no experimental evidence was provided (Tambunan et al., 2016).

A recent report predicted by molecular docking the structure of short peptides targeting the ZIKV envelope protein and the interactions between the selected peptides and virus were assessed via a fluorescence-linked sandwich immunosorbent assay (FLISA), and the performance of the peptide-linked sandwich FLISA was evaluated in virus-spiked human serum and urine (Do Thi Hoang Kim et al., 2018).

Molecular modelling is more and more used to overcome the trial and error approach and to minimize experimental problems by providing an understanding of atomic interactions and facilitating the rational design of experimental protocols (Acebes et al., 2016; Bunker et al., 2016; Singh et al., 2016; Michaeli et al., 2018; Xu et al., 2018). Virtual docking is currently an important tool in drug discovery, and a subject of important developments over the last decade (Macalino et al., 2015; Yuan et al., 2017).

However, a number of obstacles still limits the widespread use of molecular modelling for biotechnological applications. One of the most important drawbacks for mainstream use of molecular modeling is the challenge to simulate a huge number of candidates to be designed or/and docked using a full combinatorial approach.

To address this issue, herein we present a new methodology, based on an incremental construction approach to choose short peptides as binding agents for the selective detection of the intact ZIKV particles. Synthetic peptides are more resistant to physicochemical stress, more reproducible and less expensive when compared with antibodies so even if they show less specificity can be used as an array giving synergetic contribution to the detection.

Direct ELISA was chosen as the experimental protocol to check the performances of the clamp peptides. ELISA was preferred to other analytical techniques because it provides automated steps to speed-up the screening of a large number of experimental trials.

Materials and Methods

All calculations of molecular docking were done using a desktop computer with 19 processors Intel Xeon X5690 at 3.47 GHz each, with 94.5 GiB RAM, running Kernel Linux 2.6.32-642.1.1e16.x86_64, GNOME 2.28.2.

The three peptide libraries were designed and cleaned up with Hyperchem 8.0.5.

Peptides were designed in zwitterionic mode, using only the 20 natural amino acids, adding hydrogens, using molecular mechanics method amber, with the algorithm "Steepest Descents" converging at 0.08 Kj mol−1 in 32767 as maximum of cycles. Minimization, conformers generation and docking were carried out using Open Eye Scientific Software package under academic license. Each peptide library was compacted in a single file and fast minimized in gas phase to reduce computing time. In this context, solvent condition did not change significantly the results. The energy minimization process was carried out using SZYBKI 1.5.7 in its default parameterization (SZYBKI, version 1.5.7). To take into account the flexibility of the peptides, ten conformers were generated for each peptide by means of the OMEGA 2.4.6 used with MMFF as the force field (Hawkins et al., 2010; Hawkins and Nicholls, 2012; OMEGA, version 2.4.6). Therefore, the ligands were represented by the peptide conformers, around 5 millions units.

Then the envelope proteins, taken as the receptors, were downloaded from the protein data bank web site. The envelope proteins were from the flavivirus species ZIKV DENV, Chikungunya and West Nile having respectively the following codes in the Protein Data Bank web site: 5IRE, 4UTC, 3N40 and 3I50. All residues and water molecules were removed from the envelope proteins pdb files. For each envelope protein two dedicated boxes were generated, one enfolding the glycosylation site the other in the closet cavity from the glycosylation site.

In order to reduce the calculation time, tetra and pentapeptide libraries were docked using active site boxes with a volume of around 13 nm3 and hexapeptide libraries using boxes having a volume of around 18 nm3.

Using these sizes, the entire molecular surface of all peptide conformers was inside the active site box.

The active site box along with the Multi-conformer rigid body docking were carried out using OEDocking 3.0.0 (Kelley et al., 2015; OEDocking, version 3.0.0). Multi-conformer rigid body docking was run using Chemgauss4 as scoring function. The Chemgauss4, a modification of the Chemgauss3, was the latest scoring function from OpenEye software with improved hydrogen bonding and metal chelator functions. The total score obtained was the sum of steric, acceptor/metal, donor and aromatic contributions. The time required for docking a peptide library was about 24 hours.

Structures visualization and generation of molecular surfaces were performed using VIDA 4.1.1 (VIDA, version 4.1.1).

The entire process was automated using a bash script and using a freeware BASIC-like scripting language (AutoIT V3) for post processing data analysis.

Experimental Setup

All chemicals used for buffers were of analytical grade and purchased from Sigma-Aldrich (http://www.sigmaaldrich.com).

The eight clamp peptides and the four mono-arm peptides were purchased from Biomatik (http://www.biomatik.com). Cysteines within the peptide structures were used to bind maleimide-PEG2-biotin. All peptides were provided with a purity >85%.

Lyophilized peptides were diluted at 1 mM concentration in 10 mM phosphate buffered saline (PBS) pH 7.4, divided into 1004 aliquots and stored at −30° C. for further use.

Before biotin functionalization, peptides stock solution was reduced using trialkylphosphine (TCEP) from ThermoFisher Scientific (www.thermofisher.com) and after 1 h the gel was removed using TCEP gel spin separation columns (ThermoFisher Scientific). Then, 2-fold molar excess of EZ-Link™ Maleimide-PEG2-Biotin (ThermoFisher Scientific) was added to purified peptide solution and incubated for 1 h. At this concentration EZ-Link™ Maleimide-PEG2-Biotin did not contribute to background signal as shown by a pilot test using only EZ-Link™ Maleimide-PEG2-Biotin without peptide. Therefore, no further separation was carried out.

To optimize all parameters of the direct ELISA protocol, Pierce 96-Well Polystyrene Plates, (ThermoFisher Scientific) were coated overnight at 4° C. with different concentrations of intact virus particles (ZIKV or DENV). The intact virus particles were diluted using 100 mM $NaHCO_3$, pH 9.6, and aliquots of 100 μL were dispensed into each well of the plate using a multichannel pipette. This buffer pH assured a strong hydrophobic binding interaction between polystyrene and virus particles.

Intact particles both ZIKV and DENV were provided by Dr. Watkins group (University of Miami, Dep. of Pathology). The samples were controlled and counted by focus forming assay and RT-PCR, the details were reported in a previous work (Magnani et al., 2017). The Intact particles of ZIKV were inactivated using gamma irradiation. Assay biohazardous steps were carried out according to standard safety procedures.

After coating the plates overnight, the intact virus particles were removed by washing five times with the washing buffer (PBST) 10 mM PBS pH 7.4, 0.1% Tween-20, using an automated plate washer (MultiWash+, Molecular Devices, Sunnyvale, Calif.). Then, the plates were blocked with 200 μL of blocking buffers while shaking at 300 rpm at room temperature. The blocking buffers used were: Pierce™ Protein-Free (PBS) Blocking Buffer (PF), Blocker™ BLOTTO in TBS, SuperBlock™ Blocking Buffer, Blocker™ BSA (1×) in PBS. All blocking buffer were from ThermoFisher Scientific.

After 2 h the blocking buffers were removed using the same washing procedure mentioned above. 100 μL-aliquots of several dilutions of peptides biotinylated in 10 mM PBS pH 7.4 were placed in each well and incubated for 2 h while shaking at 300 rpm at room temperature. After the incubation, the unreacted peptides were removed by using the plate washer with the same settings. Then, 100 μL-aliquots of streptavidin-HRP (ThermoFisher Scientific) at a concentration of 20 ng/mL were added into each well and incubated for 30 min at room temperature without shaking. After the incubation, excess streptavidin-HRP was removed and the wells were washed with the plate washer five times using the washing buffer. Finally, 100 μL-aliquots of the Ultra TMB-ELISA Substrate Solution (ThermoFisher Scientific) were added and after 10 min the reaction was stopped by adding 100 μL aliquots of the TMB stop solution (SeraCare). The emission (450 nm) was read using a microplate reader (Clariostar Optima; BMG Labtech, Ortenberg, Germany).

The corresponding blank signals in triplicates were obtained by using all reagents without peptides. The blank signal was then subtracted to the average absorbance values for triplicate wells of each test.

All Data were processed and fitted using the software XLSTAT Version 2016.02.28451.

Results and Discussion

Docking Simulation

The envelope protein, responsible for virus entry, has very similar structure in all flavivirus. ZIKV differs from other known flavivirus by only ~10 amino acids that surround the Asn154 glycosylation site found in each of the 180 envelope glycoproteins (Sirohi et al., 2016).

Figure 1A:
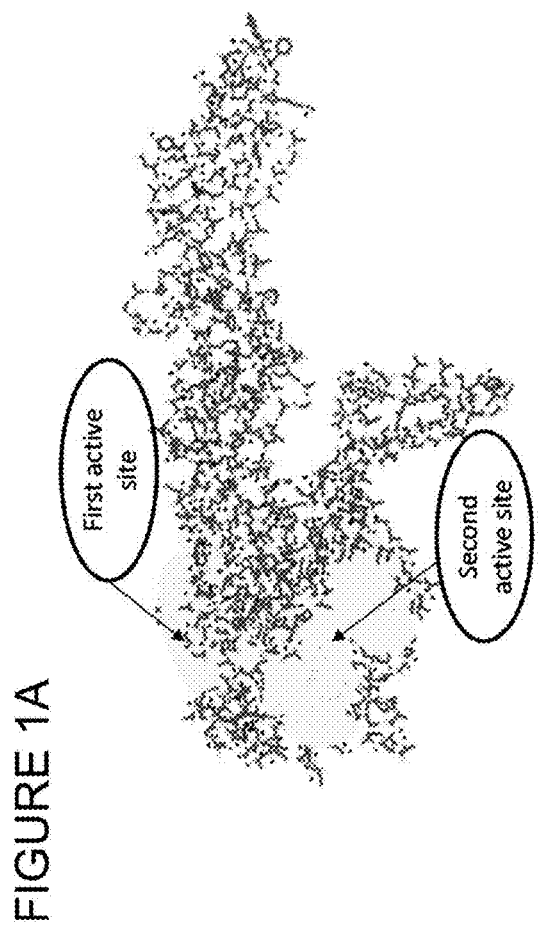
FIG. 1A is a computer-generated illustration of the target protein (ZIVA envelope protein) and the two active sites chosen for docking the peptide libraries. The larger blue shapes represent the electrostatic surfaces of the active sites.

As depicted by FIG. 1A the two arms of the clamp peptide were docked in two different envelope protein binding sites. The first active site box, defining the general space of the protein where peptides are expected to bind, was designed around the amino acid Asn 154 in the 5IRE and the amino acids Asn 153, Asn 140 and Asn 134 respectively in the 4UTC, 3N40 and 3I50. The Second active site box was built inside the closest cavity from the first active site, around the amino acid His 323 in the 5IRE and the amino acids Val 354, His 331 and His 285 respectively in the 4UTC, 3N40 and 3I50.

Figure 1D:
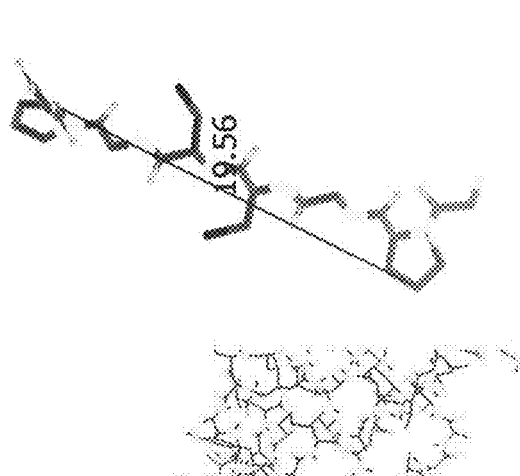
FIG. 1D is a computer-generated illustration of a bridge peptide designed and minimized in zwitterionic mode. The bridge peptide comprises eight amino acids long and has the amino acid sequence GPGCCGPG (SEQ ID NO: 32). The length in angstrom is shown (19.56 Å=1.956 nm).
Figure 1C:
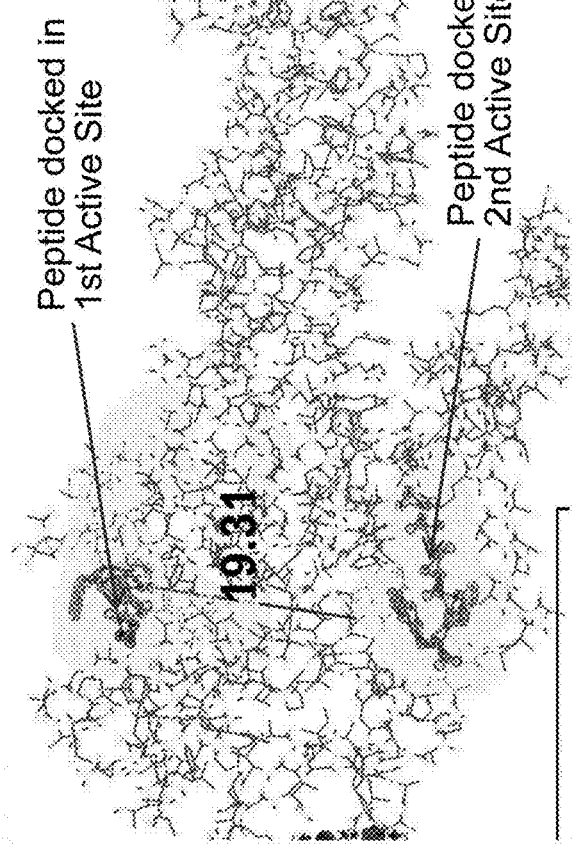
FIG. 1C is a computer-generated illustration of the target protein of FIG. 1A with two peptides (outlined in orange) docked in the two active sites. The larger blue shaded regions represent the electrostatic surfaces of the active sites. The length (in angstrom) between the two docked peptides is shown (19.31 Å or 1.931 nm) in yellow.

FIG. 1B showed the schematic representation of the clamp peptide structure made by two peptide arms of five or six amino acids in length linked by a bridge peptide having as sequence GPGCCGPG (SEQ ID NO: 32). The length in angstrom (1.931 nm) between two peptides docked in the two active sites chosen within the envelope protein was also calculated (FIG. 1C) in order to have an idea of the length needed to link the two arm peptides with a bridge peptide. The bridge peptide chosen (GPGCCGPG; SEQ ID NO: 32) had a length after minimization of 1.956 nm (FIG. 1D), approximately the distance between the two arm peptides. Using this bridge peptide size, the two arms of the clamp peptide should have enough flexibility to bind each of the two active site in synergic combination.

In order to avoid any disulfide bond between the two arms of the clamp peptide, the peptides having sulfur-containing amino acids (cysteine and methionine) were discarded during the semi-combinatorial peptide libraries screening.

The docking process was run in 3 steps. In each step a peptide library was generated by using an incremental construction approach. In every subsequent iteration, a focused library of peptides of increasing complexity, was built on previous iteration results. The first peptide library docked was made by the entire 160 k possible tetrapeptide combinations of the 20 natural amino acids.

The docking program used in this work was based on multi-conformer rigid body docking, therefore ten conformers per peptide were generated to ensure a good compromise between calculation time and accuracy of the output data for this type of ligands (Perez et al., 2013).

From the 5% peptides (8 k tetrapeptides) having the best biding score for each of the two ZIKV binding sites, only 1 k tetrapeptides were selected for the next step.

Figure 2A:
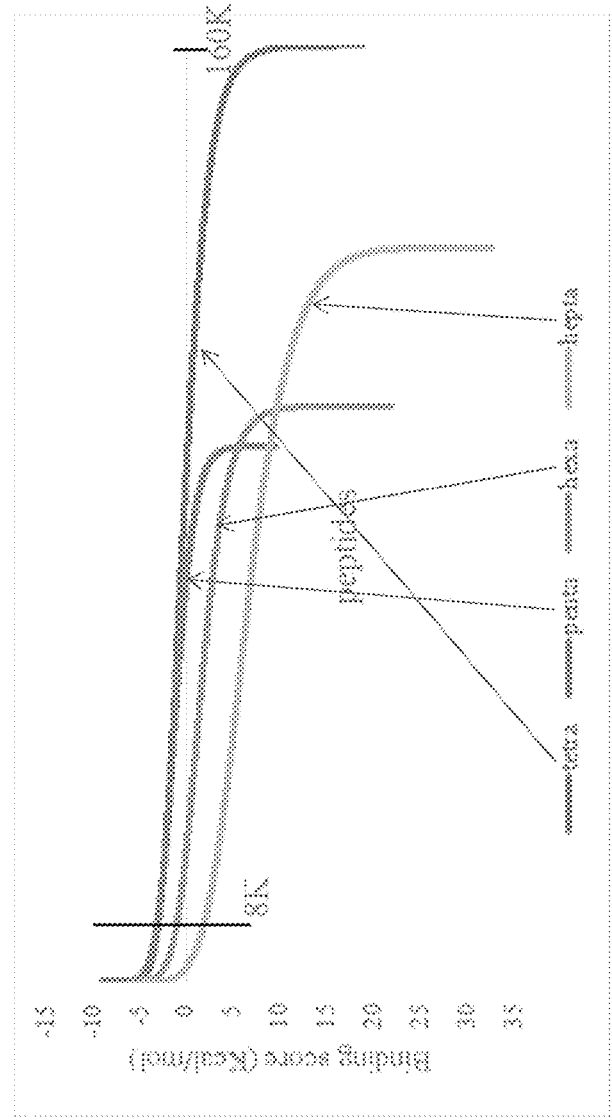
FIG. 2A is a graph of the binding score (kcal/mol) of the three peptides libraries (first library of tetrapeptides (blue); second peptide library of pentapeptides (orange); third peptide library of hexapeptides (gray)) docked in the active site 1 (Asn154), showing the typical distribution of scores obtained in the simulations. The binding score data were sorted in ascending order of binding score, thus not necessarily a correspondence must exist between the positions of the peptides in each curve.

The criterion of the selection was to choose the peptides inside the top 5% peptides binding the ZIKV active site and concurrently outside the top 5% peptides binding the other flaviviruses binding sites. The meaning of the selection was to maximize the recognition properties of the amino acid motif between the ZIKV binding site and the other flaviviruses binding sites (DENV, West Nile and Chikungunya). The 5% was selected as cutoff because in all simulations, this value delimited the zone of the curve in which the steeper slope change was observed (FIG. 2A).

This criterion was applied to the other steps to select penta, hexa and heptapeptides. FIG. 2A depicted the typical distributions of scores obtained in the simulations. The curves obtained had similar gaussian distributions. Score values comprised within the range from 20 to −10 kcal/mol in all simulations. All docking runs had approximately 5% of the complexes with higher scores and 5% with worse scores, both well separated from the rest of the population.

The score values were calculated using chemgauss4 scoring function and, thus, lower values represented higher protein-peptide affinity.

Figure 2B:
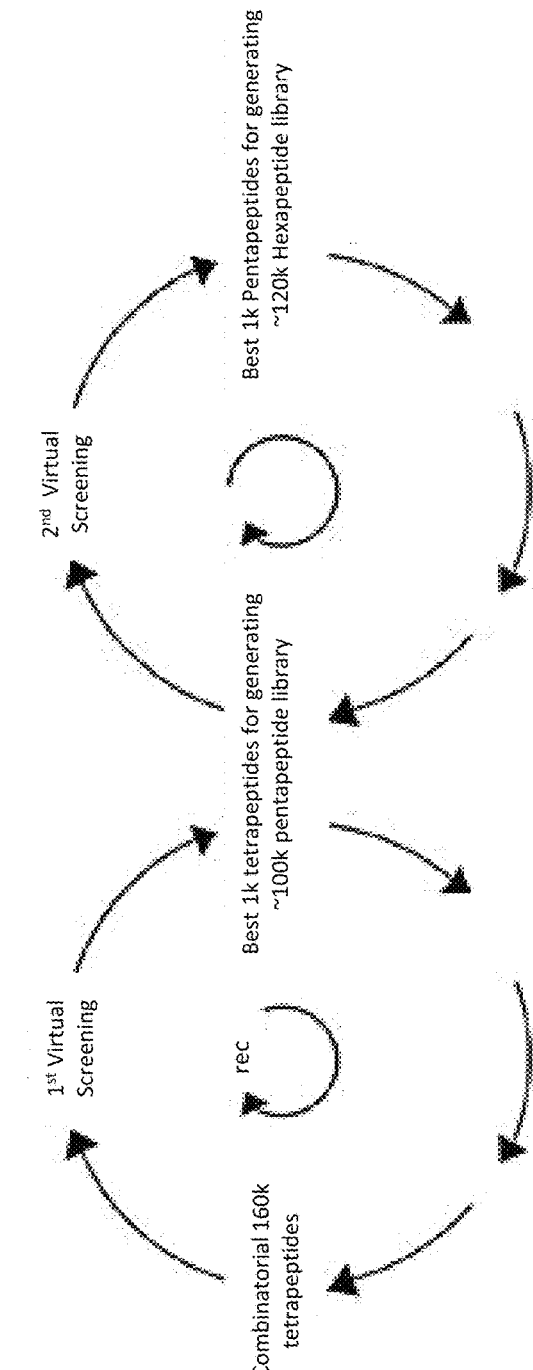
FIG. 2B is a schematic representation of the semi-combinatorial approach for obtaining penta- and hexapeptide libraries. The semi-combinatorial approach is based on generating different cycles of peptide libraries by maximizing the recognition properties of amino acid motif between the ZIKV binding site and the other flaviviruses binding sites.

The second step was the generation of the pentapeptide library by inserting each of the 20 natural amino acids in every position of the 1 k tetrapeptides selected in the previous step. As reported in FIG. 2B, the hexapeptide library was built by using the same semi-combinatorial approach carried out in the first step but selecting the best 1 k pentapeptides. A total of 380 k peptides were docked in each active site box.

Table 1 reports the statistical summary of the binding scores calculated for the three libraries of peptides towards the ZIKV envelope protein. The score values were calculated using chemgauss4 scoring function and, thus, lower values represented higher protein-peptide affinity. The peptide size played a critical role for the active site 1 interaction, with lower values decreasing drastically from pentapeptides to hexapeptides, but not for active site 2.

TABLE 1

|  | active site 1 | Active site 2 |
| --- | --- | --- |
| Tetrapeptides | | |
| min | −7.5 | −7.0 |
| max | 16.5 | 6.3 |
| Av | 0.1 | −2.2 |
| median | −0.2 | −2.2 |
| Pentapeptides | | |
| min | −9.0 | −7.0 |
| max | 9.6 | 8.1 |
| Av | −1.0 | −0.8 |
| median | −1.1 | −0.9 |
| Hexapeptides | | |
| min | −5.8 | −7.9 |
| max | 21.8 | 26.8 |
| Av | 1.9 | 2.5 |
| median | 1.6 | 2.2 |

Statistical parameters of the scores behavior (Kcal/mol), obtained using the three peptide libraries docked in the active site 1 (glycosylation binding site) and the active site 2 of the 5IRE ZIKV envelope protein.

These results could be explained considering the steric effects of the peptides within the glycosylation binding pocket. Also, the minimum-maximum dynamic range among the peptide libraries reflected that this behavior becomes relevant for hexapeptides. On the other hand, all peptide libraries showed average and median very close to each other, demonstrating a good symmetry in normal distribution.

It should be noted that the purpose of this work was to use the virtual screening step to select peptides for the specific detection of ZIKV virus among different flaviviruses.

The docking results were used to select the arms of the clamp peptides for the experimental part. This selection was based on the peptide primary structure structural analysis results along with the position in the top ranked peptides and peptide length.

The primary structural analysis of the docking results was carried out to study the occurrence of the amino acids in the top 0.1% ranked peptides that maximized the recognition properties between the ZIKV active site and the other flaviviruses binding sites (DENV, West Nile and Chikungunya).

One peptide with high and one with low occurrence amino acids in primary structure were then chosen within the 0.1% top ranked peptides binding each of the two envelope protein active sites. The four peptides were selected from both penta and hexapeptide libraries, resulting in a total of 8 peptides, four pentapeptides and four hexapeptides.

Table 2 reports the results of the amino acid occurrence (%) in the primary structure of the eight peptides selected to build the clamp peptides. The occurrence was calculated counting the recurrence of each amino acid in the relative position (five positions for pentapeptides and six positions for hexapeptides) in the top 0.1% ranked peptides binding the active site 1 and 2 of the ZIKV envelope protein. The best occurrence amino acids were also reported, but peptides having all best occurrence amino acids were not present or were in the bottom of the 0.1% top rank peptides.

TABLE 2

Amino acid occurrence in the top 160 ranked peptides (%)

|  |  | 1P | 2P | 3P | 4P | 5P | Average |
|---|---|---|---|---|---|---|---|
| Active site 1 | SWPGQ (24) | 24.4 | 13.8 | 22.5 | 34.4 | 1.3 | 19.3% |
|  | LRGHA (25) | 11.3 | 8.1 | 21.9 | 21.3 | 7.5 | 14.0% |
|  | best occurrence AA: SMAGG (37) | *24.4* | *14.4* | *31.3* | *34.4* | *18.8* | *24.6%* |
| Active site 2 | WPHTQ (16) | 58.8 | 63.1 | 15.0 | 4.4 | 10.0 | 30.3% |
|  | AGRRP (20) | 5.0 | 4.4 | 9.4 | 6.3 | 28.1 | 10.6% |
|  | best occurrence AA: WPFFP (38) | *58.8* | *63.1* | *20.0* | *13.1* | *28.1* | *36.6%* |

|  |  | 1P | 2P | 3P | 4P | 5P | 6P | Average |
|---|---|---|---|---|---|---|---|---|
| Active site 1 | KRNATP (26) | 10.0 | 6.3 | 28.8 | 56.9 | 34.4 | 41.9 | 29.7% |
|  | KTDAYS (27) | 10.0 | 10.0 | 3.1 | 56.9 | 2.5 | 3.8 | 14.4% |
|  | best occurrence AA: GPNATP (39) | *14.4* | *11.9* | *28.8* | *56.9* | *34.4* | *41.9* | *31.4%* |
| Active site 2 | WPWIGT (18) | 75.0 | 80.0 | 32.5 | 13.1 | 35.6 | 8.8 | 40.8% |
|  | MDSPIK (22) | 1.3 | 0.6 | 1.3 | 2.5 | 1.9 | 2.5 | 1.7% |
|  | best occurrence AA: WPWFGP (40) | *75.0* | *80.0* | *32.5* | *27.5* | *35.6* | *18.8* | *44.9%* |

Analysis of the amino acid occurrence (%) in the primary structure of the eight peptides selected to build the eight clamp peptides. The occurrence was calculated counting the recurrence of each amino acid in the relative position (five positions for pentapeptides and six positions for hexapeptides) in the top 0.1% ranked peptides binding the active site 1 and 2 of the ZIKV envelope protein. The best occurrence amino acids were also reported (in italic) along with the average (Av) percentage of the occurrence for each peptide. SEQ ID NO: noted in ( ).

In the active site 1 of ZIKV envelop protein (glycosylation active site), the pentapeptide SWPGQ (SEQ ID NO: 24) and hexapeptide KRNATP (SEQ ID NO: 26) had almost all amino acids with high occurrence with some exception, the glutamine in fifth position for SWPGQ (SEQ ID NO: 24) and lysine in second position for KRNATP (SEQ ID NO: 26). The average in percentage of the occurrence (19.3% and 29.7%) was the highest of the top 0.1% ranked peptides in their respective libraries.

The other pentapeptide LRGHA (SEQ ID NO: 25) had amino acids with about half percentage of occurrence when compared to the top one in almost all the five positions. On the other hand, the hexapeptide KTDAYS (SEQ ID NO: 27) showed and alternate low and high occurrence percentage.

The penta and hexapeptides selected from the active site 2 docking, had similar high and low average occurrence amino acids in primary structure. Remarkably, the hexapeptides WPWIGT (SEQ ID NO: 18) and MDSPIK (SEQ ID NO: 22) had respectively the highest and lowest amino acids occurrence (40.8% and 1.7%) of the peptides selected to build the clamp peptides.

Table 3 shows the relative docking score position in the corresponding libraries of the eight peptides chosen to build the arms of the clamp peptides tested in the experimental evaluation. The ranking scores between the ZIKV sites and the other flaviviruses binding sites were for all peptides different enough to expect a ZIKV selective binding. Nevertheless, only three peptides ranked in the first 10 best peptides in binding ZIKV, highlighting strong similarities between the flaviviruses glycosylation sites. It should be noted that in all peptide libraries the simulated binding energy decreased exponentially in the top 1% best ranked peptides, in fact, a decrease of at least 20% in the binding score is observed for the $100^{th}$ peptide position.

TABLE 3

| Peptide (SEQ ID NO:) | ZIKV | DENV | West Nile | Chikungunya |
|---|---|---|---|---|
| Active site 1 Docking score rank | | | | |
| LRGHA (25) | 53 | 74900 | 69645 | 71784 |
| SWPGQ (24) | 4 | 55575 | 27840 | 47111 |
| KRNATP (26) | 16 | 85123 | 100716 | 74427 |
| KTDAYS (27) | 125 | 95558 | 110693 | 86882 |
| Active site 2 Docking score rank | | | | |
| WPHTQ (16) | 9 | 47135 | 43238 | 45072 |
| AGRRP (20) | 13 | 29265 | 51031 | 18894 |
| WPWIGT (18) | 1 | 21334 | 9821 | 18311 |
| MDSPIK (22) | 46 | 10080 | 40000 | 7831 |

Relative docking score position of the four pentapeptides and four hexapeptides selected for building the eight clamp peptides. The ranking obtained from the two active sites of the ZIKV envelope protein was compared to the one obtained using the other three flaviviruses envelope proteins.

The four pentapeptides and four hexapeptides were then combined to build eight clamp peptides. At this stage a mix between penta and hexapeptides was avoided in order to understand the contribution of the peptide length in the experimental responses.

Table 4 reports the physicochemical properties of the peptides selected for experimental evaluation. The peptides were the eight clamp peptides built using the combination of the penta or hexapeptides, and the mono-arm peta and hexapeptides binding the ZIKV envelope protein glycosylation binding site. Cysteine was inserted in the bridge of clamp peptides and at the N-terminus of mono-arm peptides to bind the maleimide-PEG2-biotin used to label each of the peptides with the signal amplifier streptavidin-HRP.

TABLE 4

| Active site 2* | Bridge Peptide* | Active site 1* | Label | Iso-Point pH | net charge pH7 | Water Sol | MW |
|---|---|---|---|---|---|---|---|
| WPHTQ (16) | GPGCCG (32) | PGSWPGQ (24) | C1 | 6.9 | 0.0 | poor | 1852 |
| WPHTQ (16) | GPGCCG (32) | PGLRGHA (25) | C2 | 8.1 | 1.1 | poor | 1831 |
| WPWIGT (18) | GPGCCGPG (32) | KRNATP (26) | C3 | 8.9 | 1.9 | poor | 2055 |
| WPWIGT (18) | GPGCCGPG (32) | KTDAYS (27) | C4 | 5.8 | -0.1 | poor | 2053 |
| AGRRP (20) | GPGCCGPG (32) | SWPGQ (24) | C5 | 12.1 | 2.0 | good | 1739 |
| AGRRP (20) | GPGCCGPG (32) | LRGHA (25) | C6 | 10.6 | 3.0 | good | 1718 |
| MDSPIK (22) | GPGCCGPG (32) | KRNATP (26) | C7 | 8.8 | 1.9 | good | 1986 |
| MDSPIK (22) | GPGCCGPG (32) | KTDAYS (27) | C8 | 5.9 | -0.1 | good | 1984 |
|  |  | C-SWPGQ (33) | P1 | 3.0 | -0.1 | poor | 676 |
|  |  | C-LRGHA (34) | P2 | 9.2 | 1.0 | good | 655 |
|  |  | C-KRNATP (35) | X1 | 10.5 | 1.9 | good | 788 |
|  |  | C-KTDAYS (36) | X2 | 5.9 | -0.1 | good | 786 |

Physicochemical properties of the eight peptides selected for experimental part.
A cysteine was added to the N terminus of each mono-arm peptide to link the maleimide-PEG2-biotin.
*SEQ ID NOs: are noted in ( ).

The experimental analysis was performed in PBS at pH 7.4. Therefore, the physicochemical properties were focused on water solubility and net charge at pH 7. The first four clamp peptides and one of the mono-arm pentapeptide had poor water solubility due to the ratio of the hydrophobic amino acids, but when they were used at micromolar concentration were able to be dissolved in PBS. Five clamp peptides and two mono-arm peptides had a significant amount of positively charged amino acids resulting in a positive net charge at pH 7. Due to the presence of the polar amino acids the other peptides had a slightly negative net charge at pH 7.

Moreover, to highlight the positive or negative charges inside the peptide, the pH of the isoelectric point of each peptide was also reported. Interestingly, the majority of peptides selected had positively charged amino acids improving the possibility to interact with negative charges in the three-dimensional structure of both ZIKV binding sites selected.

Experimental Results

The eight clamp peptides and the four mono-arm peptides selected, were tested vs intact ZIKV particles by using a direct ELISA. The peptides were biotinylated by using the maleimide-PEG2-biotin reagent that reacts with the sulfhydryl group of the cysteine efficiently and specifically by forming a stable thioether bond. The antibody 4G2 hybridoma mouse IgG2a was used as the reference and employed in combination with an anti-mouse IgG conjugated to HRP.

All analytical parameters involved in the development of ELISA were optimized by using 96-well plates coated with triplicate 10-fold serial dilutions of intact ZIKV particles. The results were reported in Table 5.

TABLE 5

|  |  | C1 | C2 | C3 | C4 | C5 | C6 | C7 | C8 | P1 | P2 | X1 | X2 | AB 4G2 |
|---|---|---|---|---|---|---|---|---|---|---|---|---|---|---|
| Blocking Incubation buffer |  | BT PBST | BT PBST | BT PBST | BT PBST | PF PBST | PF PBST | PF PBST | PF PBST | PF PBS | PF PBS | PF PBS | PF PBS | PF PBST |
| FPLR Dynamic Range | (log[ZIKV], copies/mL) | 5-7 | 5-7 | 4-7 | 6-7 | 6-7 | 4-7 | 4-7 | 5-7 | 7-8 | 5-7 | 5-7 | 6-8 | 6-8 |
| LOD | (log[ZIKV], copies/mL) | 4.8 | 4.5 | 3.5 | 5.7 | 5.8 | 3.5 | 3.7 | 4.7 | 6.8 | 4.5 | 4.8 | 5.8 | 5.8 |
| FPLR C50 | (log[ZIKV], copies/mL) | 6.3 | 6.2 | 5.3 | 6.3 | 6.4 | 5.2 | 5.8 | 6.2 | nd | 6.2 | 6.1 | 6.1 | 6.2 |
| FPLR slope | $\Delta A$/(log[ZIKV]) | 33.2 | 25.4 | 8.7 | 32.8 | 25.6 | 10.1 | 5.3 | 33.9 | nd | 19.9 | 20.8 | 27.7 | 22.3 |
| FPLR maximum | $\Delta A$ | 0.43 | 0.55 | 0.67 | 0.40 | 0.17 | 0.53 | 0.95 | 0.82 | nd | 0.94 | 0.98 | 0.91 | 0.81 |
| FPLR minimum | $\Delta A$ | 0.03 | 0.05 | 0.05 | 0.02 | 0.01 | 0.05 | 0.01 | 0.03 | nd | 0.04 | 0.03 | 0.01 | 0.04 |
| FPLR $R^2$ |  | 0.98 | 1.00 | 0.99 | 1.00 | 0.97 | 0.99 | 0.99 | 0.99 | nd | 0.99 | 1.00 | 1.00 | 0.99 |
| Peptide Concentration | (μM) | 2 | 2 | 0.5 | 2 | 5 | 0.5 | 5 | 5 | 20 | 20 | 20 | 20 | 1 □g/ml |
| Intra-day reproducibility | CV(%) | <5 | <5 | <7 | <5 | <4 | <7 | <4 | <4 | <5 | <5 | <5 | <5 | <10 |

TABLE 5-continued

|  |  | C1 | C2 | C3 | C4 | C5 | C6 | C7 | C8 | P1 | P2 | X1 | X2 | AB 4G2 |
|---|---|---|---|---|---|---|---|---|---|---|---|---|---|---|
| Inter-day and batch-to-batch reproducibility | CV(%) | <12 | <12 | <15 | <12 | <10 | <15 | <10 | <10 | <10 | <10 | <10 | <10 | nd |
| Long-term stability | (Month) | >1 | >1 | >1 | >1 | >1 | >1 | >1 | >1 | >1 | >1 | >1 | >1 | nd |
| Assay time after Plate Coating | (h) | 5 | 5 | 5 | 5 | 5 | 5 | 5 | 5 | 5 | 5 | 5 | 5 | 8 |

Optimized experimental parameters of the direct ELISA assay for the eight clamp peptides, the four mono-arm peptides and a commercial antibody (4G2).
BT = BLOTTO blocking buffer;
PF = protein free blocking buffer;
PBS = 10 mM phosphate buffer saline pH 7.4;
PBST = 10 mM PBS pH 7.4, 0.1% Tween-20.
FLRP = Four Parameter Logistic Regression To minimize nonspecific binding, four blocking agents (PF, BLOTTO, SuperBlock™ Blocking Buffer, Blocker™ BSA) were tested. All blocking agents had very low background signal. For hydrophilic peptides the lowest background signal was achieved using PF that gave the best performances also using the antibody 4G2. For hydrophobic peptides, the blocker BLOTTO showed better performance, except for mono-arm peptide P1.

For clamp peptides and antibody, the surfactant agent tween 20 at 0.1% was necessary in the incubation step. No longer than one hour was necessary for peptide incubation, a longer time increased both the overall signal generated by the binding event and the background signal. Shacking during incubation improved the signal to noise ratio.

The optimal concentration of peptide was determined by coating clear 96-well plates with a solution of $10^{\wedge 7}$ copies/mL of intact ZIKV particles. Concentrations of peptide, from 0.1 to 50 µM, diluted in 10 mM PBS pH 7.4 were added to wells of the microplates coated with intact ZIKV particles. For mono-arm peptides, larger concentrations than 20 µM did not increase the assay sensitivity.

Clamp peptides showed higher sensitivity than mono-arm peptides. Clamp peptides C5, C7 and C8 showed the best performances when used at 5 µM. The clamp C1, C2 and C4 at concentration of 2 µM did the best signal to noise ratio. Impressively, clamp peptides C3 and C6 had be used at concentration of 0.5 µM to have the best results, highlighting the remarkable high sensitivity of those peptides in this kind of assay.

Thus, the peptide concentrations reported in Table 5 were used to estimate the dynamic range and the LOD of the assay by using 10-fold serial dilutions of intact ZIKV particles from $10^{\wedge 1}$ to $10^{\wedge 8}$ copies/mL.

The results had a sigmoidal ZIKV particles concentration response and the calibration curves were obtained by plotting the delta absorbance (after blank signal subtraction) against the log of ZIKV particles concentration and fitting the experimental data with a four-parameter logistic function (FPLR).

Figure 3:
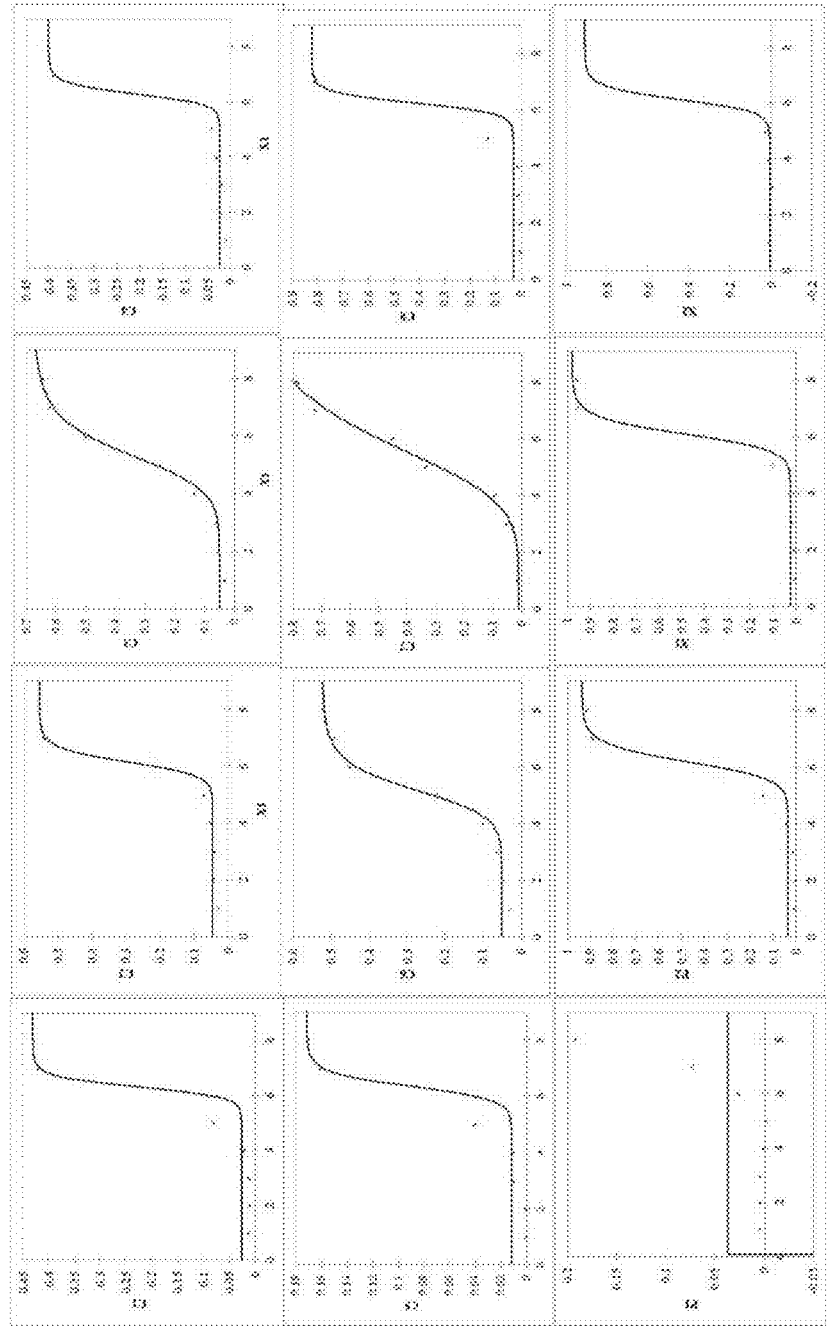
FIG. 3 is a series of graphs depicting the sigmoidal ZIKV particles concentration response trend. Y axis=A absorbance (450 nm); X-axis=log [ZIKV], copies/mL.

The regression parameters of the assay were reported in Table 5 and the sigmoidal trend in FIG. 3. The LOD was interpolated from the calibration curves using LOD=$S_B$+3× $SD_B$ where $S_B$ and $SD_B$ were the average and the standard deviation of the blank measurements, respectively.

Dose-response curves generated with all peptides and the antibody had at least two-order of magnitude dynamic range except for peptide P1, which had just a one order of magnitude dynamic range.

The peptide based assay using C3, C6, and C7 showed three-order of magnitude dynamic range and lower detection limits with dynamic range starting from $10^{\wedge 4}$ copies/mL one or two order magnitude lower than the others peptides or antibody based assay. The better performance in binding ZIKV intact particles by those three clamp peptides was also highlighted by the FPLR C50 parameter. The dose-response performance of the assay was reproducible over a month (RSD lower than 15%), demonstrating that the peptides had high stability and reproducibility.

The cross-reactivity among Flaviviruses is a key parameter to be tested for this assay. Using the same ELISA protocol, the three clamp peptides (C3, C6 and C7) with higher sensitivity versus the intact ZIKV particles where employed to test the ability to discriminate ZIKV from the three serotypes of DENV (DENV-1, -2 and -3). The cross reactivity performances were compared with that obtained using the mono-arm peptides P2 and X1, that showed the best analytical parameters within the mono-arm peptides.

Figure 4:
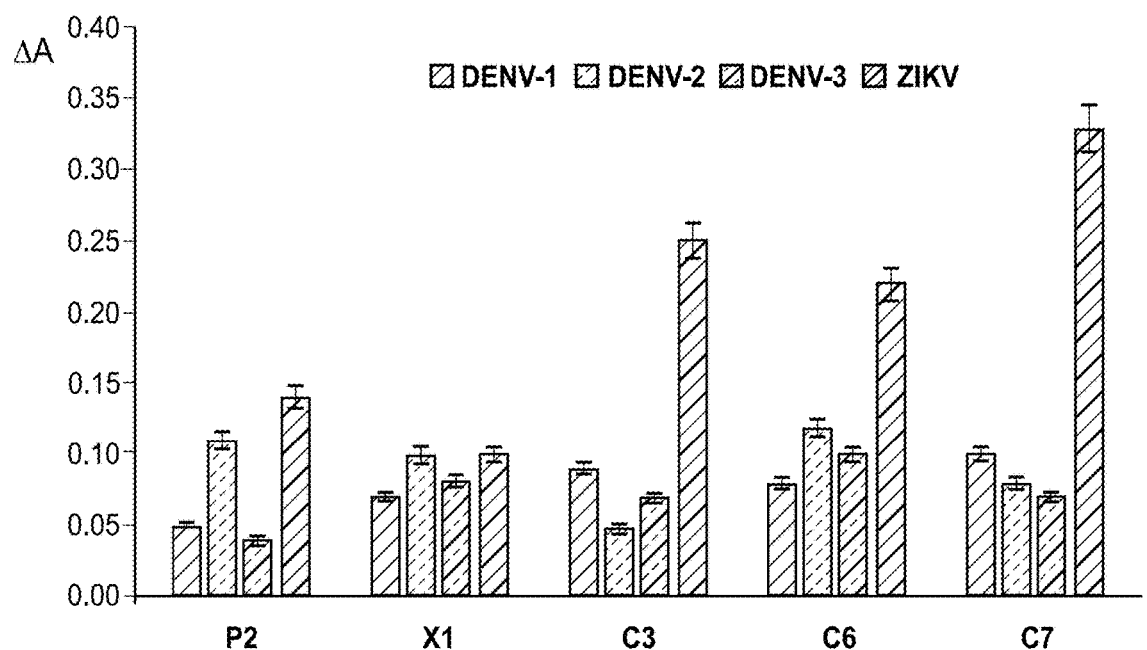
FIG. 4 is a graph of the A spectrophotometric absorbance signals obtained in a cross-reactivity study using the ELISA direct assay for the best three clamp peptides (C3, C6 and C7) and two mono-arm peptides (P2 and X1) binding the ZIKV target protein (yellow) and three serotypes of DENV virus (DENV-1 (blue), DENV-2 (orange) and DENV-3 (grey)) at the concentration of $10^5$ [ZIKV] copies/mL.
Figure 5:
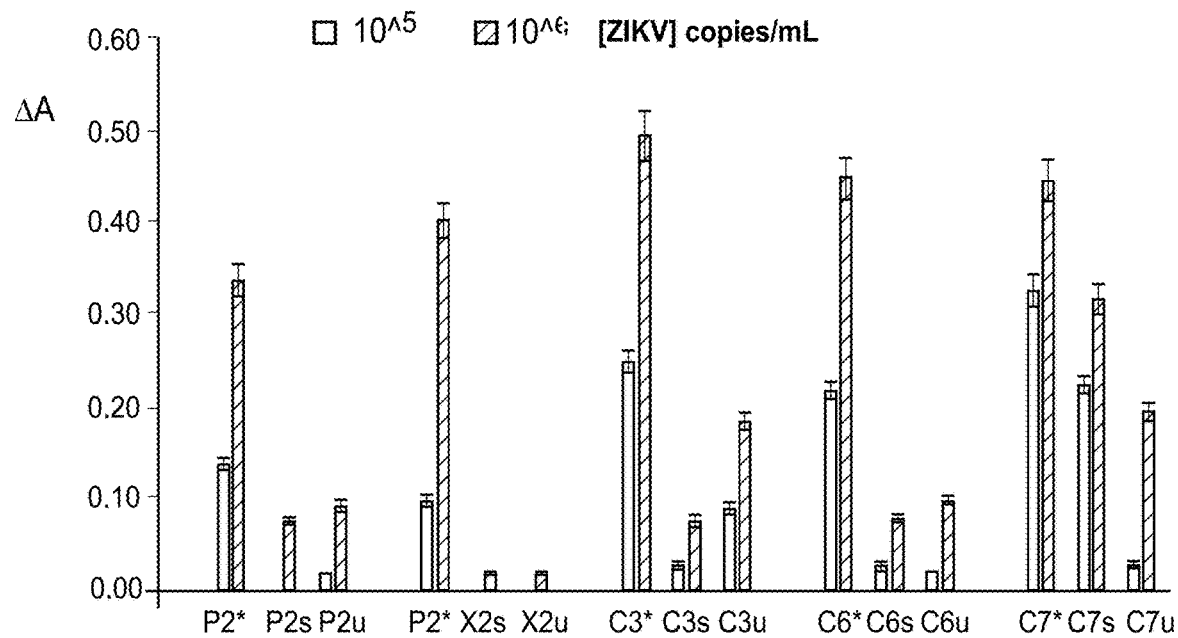
FIG. 5 is a graph of the A spectrophotometric absorbance signals obtained in a study using the ELISA direct assay for the best three clamp peptides (C3, C6 and C7) and two mono-arm peptides (P2 and X1) binding the ZIKV target protein at a concentration of $10^5$ copies/ml (blue) or $10^6$ copies/mL (orange) in the presence of buffer (*), serum (s), or urine (u).

The results shown in FIG. 4 were obtained by coating clear 96-well plates with a solution of $10^{\wedge 5}$ copies/mL of intact virus particles. At this concentration, all three peptides showed slight cross-reactivity against the DENV. Clamp peptides C3 and C7 had the higher DENV/ZIKV signal ratio with around 70% signal decrease for all DENV serotypes. Clamp Peptide C6 showed slight cross reactivity with DENV-2 and DENV-3 with only 45% and 55% of signal decrease respectively. The three clamp peptides clearly discriminated between the two flavivirus species. At this concentration, mono-arm peptide assays had the ZIKV delta absorbance signals statistically comparable to the signals obtained using DENV.

Nevertheless, it should be highlight that increasing the coating concentration of the virus to $10^{\wedge 6}$ copies/mL the ZIKV and DENV analytical signals were statistically equivalent, losing, for the clamp peptides, the discrimination between ZIKV and DENV.

Usually, the presence of ZIKV in affected bodies is detected in biological fluids. Therefore, the analytical sensitivity of the selected peptides was tested in two biological matrices, namely, urine and serum. The matrix effect was investigated to understand how real biological fluids could modify the binding efficiency of the peptides.

FIG. 4 depicts the ELISA data using solutions of peptides with or without the urine and serum obtained coating clear 96-well plates with $10^{\wedge 5}$ and $10^{\wedge 6}$ copies/mL of intact ZIKV particles. Urine and serum were 1:1 and 1:10 diluted, respectively, with a concentrated peptide PBS solution (10 mM PBS, pH 7.4) to obtain a peptide final concentration of 0.5 µM for C3 and C6, 5 µM for C7 and 20 µM for mono-arm peptides (P2 and X1).

Clamp peptide C3 showed a better performance in urine than serum, particularly for $10^{\wedge 5}$ copies/mL. Clamp peptide C6 had a strong decrease in the signal generated at both $10^{\wedge 5}$ or $10^{\wedge 6}$ copies/mL in both urine and serum. Clamp peptide C7 exhibited the best performance among the three clamp peptides, having higher signals in serum than in urine. All clamp peptides lost at the least one order of magnitude signal detecting ZIKV in urine or serum, except for C7 in serum, having a distinct analytical signal also at $10^{\wedge 5}$ copies/mL of ZIKV.

Mono-arm peptides lost completely the signal at $10^{\wedge 5}$ copies/mL of ZIKV, starting to detect ZIKV particles in both urine or serum, from $10^{\wedge 6}$ copies/mL using P1 and from $10^{\wedge 7}$ copies/mL using X1 (data not showed).

It should be highlighted that when a body is under a ZIKV infection the level of flavivirus concentration in urine can be up to $10^{6.9}$ copies/mL (Campos et al., 2016; Pawley et al., 2019).

CONCLUSIONS

The semi combinatorial virtual strategy to design clamp peptides using the two flavivirus active sites as a binding target has shown to have the potential for designing antibody mimetics for the selective detection of ZIKV.

The ELISA assay platform developed for testing the newly designed clamp peptides offered the possibility to optimize in short time the experimental conditions for evaluation of the eight clamp peptides and four mono-arm peptides chosen from the most promising ones yield by the in-silico studies. The three clamp peptides with better performances to detect ZIKV had shown to have also semi-selective properties when tested against DENV. The matrix-effect was also investigated, by testing the response of the peptides in physiological matrices, i.e., urine and serum. We observed that the matrix affected the assay performance by decreasing the detection limits by one order of magnitude, albeit still having a distinct analytical signal starting from $10^6$ copies/mL, the concentration of ZIKV in acute infection.

This work represents a new methodology for the selection of tailor-made clamp peptides, rationalizing the way to choose receptors with high binding ability among thousands of potential compounds that can be employed in biotechnology, medical, and a variety of analytical applications. Taking advantage of the fast progress in computing, we envision that it will be possible to simulate in short time the clamp peptides having even more complex shapes with better selectivity and less cross-reactivity.

REFERENCES

Acebes et al., *ACS Catalysis* 6(3), 1624-1629 (2016).

Barba-Spaeth et al., *Nature* 536(7614), 48. (2016).

Bunker et al., *Biochimica et Biophysica Acta (BBA)-Biomembranes* 1858(10), 2334-2352 (2016).

Campos et al., *Journal of Clinical Virology* 77, 69-70 (2016).

Do Thi Hoang Kim et al., *Theranostics* 8(13), 3629 (2018).

Gong et al., *Yi Chuan* 32(6), 548-554 (2010).

Hawkins et al., *Journal of Chemical Information and Modeling* 52(11), 2919-2936. doi: 10.1021/ci300314k.

Hawkins et al., *Journal of Chemical Information and Modeling* 50(4), 572-584. doi: 10.1021/ci100031x. (2010)

Heffron et al., *PLoS neglected tropical diseases* 12(11), e0006903 (2018).

Hwang et al., *Biosensors and Bioelectronics* 87, 164-170 (2017).

Ioos et al., *Medecine et maladies infectieuses* 44(7), 302-307 (2014).

Kelley et al., POSIT: flexible shape-guided docking for pose prediction. *Journal of chemical information and modeling* 55(8), 1771-1780 (2015).

Li et al., Electrochemical aptamer-based sensors for food and water analysis: A review. *Analytica chimica acta*. (2018)

Lin et al., *Journal of Chromatography A* 1446, 34-40 (2016).

Macalino et al., *Archives of pharmacal research* 38(9), 1686-1701 (2015).

Magnani et al., *Science translational medicine* 9(410), eaan8184 (2017).

Mascini et al., *Biosensors and Bioelectronics* 123, 124-130 (2019).

Mascini et al., *Talanta* 167, 126-133 (2017).

Michaeli et al., *The Journal of Immunology* 201(11), 3383-3391 (2018).

OEDocking. version 3.0.0. OpenEye Scientific Software, Santa Fe, N. Mex. http://www.eyesopen.com.

OMEGA. version 2.4.6. OpenEye Scientific Software, Santa Fe, N. Mex. http://www.eyesopen.com.

Palzkill et al., U.S. patent application Ser. No. 14/777,714), (2018)

Pawley et al., *ACS Omega* 4(4), 6808-6818 (2019).

Perez et al., Peptides trapping dioxins: a docking-based inverse screening approach. *Journal of Chemistry* 2013.

Pichon et al., *Anal Bioanal Chem* 407(3), 681-698. doi: 10.1007/s00216-014-8129-5 (2015).

Priyamvada et al., *Proceedings of the National Academy of Sciences* 113(28), 7852-7857 (2016).

Singh et al., *Journal of medicinal chemistry* 59(8), 3920-3934 (2016).

Sirohi et al., *Science* 352(6284), 467-470 (2016).

Stettler et al., *Science* 353(6301), 823-826 (2016).

Stobiecka et al., *Chemical Papers* 69(1), 62-76 (2015).

SZYBKI. version 1.5.7. OpenEye Scientific Software, Santa Fe, N. Mex. http://www.eyesopen.com.

Tambunan et al., *Jurnal Teknologi* 78(4-3) (2016).

Tang et al., *Talanta* 146, 55-61 (2016).

VIDA. version 4.1.1. OpenEye Scientific Software, Santa Fe, N. Mex. http://www.eyesopen.com.

Weaver et al., *Antiviral research* 130, 69-80 (2016).

Xu et al., *Nature medicine* 24(6), 857 (2018)

Yu et al., *Annual Review of Analytical Chemistry* 10, 293-320 (2017).

Yuan et al., *Wiley Interdisciplinary Reviews: Computational Molecular Science* 7(2), e1298 (2017).

Zhao et al., Structural basis of Zika virus-specific antibody protection. *Cell* 166(4), 1016-1027 (2016).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the disclosure (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted.

Recitation of ranges of values herein are merely intended to serve as a shorthand method of referring individually to each separate value falling within the range and each endpoint, unless otherwise indicated herein, and each separate value and endpoint is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

Preferred embodiments of this disclosure are described herein, including the best mode known to the inventors for carrying out the disclosure. Variations of those preferred embodiments may become apparent to those of ordinary skill in the art upon reading the foregoing description. The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

What is claimed:

1. A method implemented by a processor in a computer for iteratively designing a linear clamp peptide that binds to two different binding sites of a target protein, wherein the linear clamp peptide comprises the structure $A_1$-B-$A_2$ wherein $A_1$ is a first peptide arm of the linear clamp peptide binds to a first binding site of a target protein, $A_2$ is a second peptide arm of the linear clamp peptide binds to a second binding site of the target protein, and B is a bridge peptide which links $A_1$ to $A_2$, the iterative designing method comprising the steps of:
  (a) determining a binding score of each tetrapeptide of a first peptide library for the first binding site of the target protein, wherein the first peptide library comprises a full combinatorial set of 160 K tetrapeptides having a combination of four amino acids of the twenty naturally-occurring amino acids,
  (b) identifying the sequences of the tetrapeptides having a binding score for the first binding site of the target protein which meets a first threshold, wherein the first threshold is a score of binding between each tetrapeptide and a first active site of the target protein;
  (c) determining a binding score of each pentapeptide of a second peptide library for the first binding site of the target protein, wherein the second peptide library comprises a set of pentapeptides having a combination of five amino acids comprising the amino acids of the sequence of a tetrapeptide identified in step (b) and one of the twenty naturally-occurring amino acids added as the first amino acid or the fifth amino acid of the pentapeptide or between two amino acids of the sequence of the tetrapeptide,
  (d) identifying the sequences of the pentapeptides having a binding score for the first binding site of the target protein which meets a second threshold, wherein the second threshold is a score of binding between each pentapeptide and a first active site of the target protein,
  (e) determining a binding score of each hexapeptide of a third peptide library for the first binding site of the target protein, wherein the third peptide library comprises a set of hexapeptides having a combination of six amino acids comprising the amino acids of the sequence of a pentapeptide identified in step (d) and one of the twenty naturally-occurring amino acids added as the first amino acid or the sixth amino acid of the hexapeptide or between two amino acids of the sequence of the pentapeptide, (f) identifying the sequences of the hexapeptides having a binding score for the first binding site of the target protein which meets a third threshold, wherein the third threshold is a score of binding between each hexapeptide and a first active site of the target protein, (g) repeating steps (a), (c) and (e) to determine a binding score for the second binding site of the target protein for each tetrapeptide of the first peptide library, for each pentapeptide of the second peptide library, and for each hexapeptide of the third peptide library;

(h) repeating steps (b), (d), and (f) to identify the sequences of the tetrapeptides, pentapeptides and hexapeptides having a binding score for the second binding site of the target protein which meets a first, second, and third threshold, wherein the first threshold is a score of binding between each tetrapeptide and a second active site of the target protein, wherein the second threshold is a score of binding between each pentapeptide and a second active site of the target protein, and wherein the third threshold is a score of binding between each hexapeptide and a second active site of the target protein;

(i) selecting the A1 peptide arm based on peptides identified as having a binding score for the first binding site of the target protein that meets the first, second and third threshold, (j) selecting the A2 peptide arm based on peptides identified as having a binding score for the second binding site of the target protein that meets the first, second and third threshold, (k) generating the linear clamp peptide, wherein the linear clamp peptide comprises the A1 peptide selected in step (i) and the A2 peptide selected in step (i).

2. The method of claim 1, comprising generating the first peptide library, the second peptide library, the third peptide library, and/or the fourth peptide library.

3. The method of claim 1, wherein the first peptide library comprises 160,000 tetrapeptides.

4. The method of claim 1, wherein the first threshold is the top 5% of binding scores, and wherein 8000 sequences of tetrapeptides are identified upon step (b).

5. The method of claim 1, wherein the first threshold is the top 5% of binding scores and a binding score outside the top 5% of binding scores for a different target protein, and wherein 1000 sequences of tetrapeptides are identified upon step (b).

6. The method of claim 1, wherein the second threshold is the top 5% of binding scores, and wherein the second threshold further comprises a binding score outside the top 5% of binding scores for a different target protein.

7. The method of claim 1, wherein the third threshold is the top 5% of binding scores, and wherein the third threshold further comprises a binding score outside the top 5% of binding scores for a different target protein.

8. The method of claim 1, wherein binding scores are calculated using a docking scoring function.

9. The method of claim 1, wherein the binding scores for more than 350,000 peptides are determined for each of the first binding site and the second binding site.

10. The method of claim 1, further comprising determining the length of B of the clamp peptide by measuring the distance between a peptide bound to the first binding site of the target protein and a peptide bound to the second binding site of the target protein.

11. The method of claim 1, wherein binding scores are determined using a molecular docking program.

12. The method of claim 11, wherein the molecular docking program is based on multi-conformer rigid body docking, which evaluates 10 conformers per peptide.

13. The method of claim 8, wherein the docking scoring function is chemgauss4.

14. A method of manufacturing a linear clamp peptide that binds to two different binding sites of a target protein, wherein the linear clamp peptide comprises the structure $A_1$-B-$A_2$ wherein $A_1$ is a first peptide arm that binds to a first binding site of a target protein, $A_2$ is a second peptide arm that binds to a second binding site of the target protein, and B is a bridge peptide which links $A_1$ to $A_2$, said method comprising iteratively designing the first peptide arm and the second peptide arm of the clamp peptide according to the method of claim 1 and joining the first peptide arm to the second peptide arm with a bridge peptide, B.

* * * * *

SEQUENCE LISTING

```
<160> NUMBER OF SEQ ID NOS: 40

<210> SEQ ID NO 1
<211> LENGTH: 672
<212> TYPE: PRT
<213> ORGANISM: Zika virus
<300> PUBLICATION INFORMATION:
<308> DATABASE ACCESSION NUMBER: GenBank / KU926309.1
<309> DATABASE ENTRY DATE: 2016-03-21
<313> RELEVANT RESIDUES IN SEQ ID NO: (1)..(672)

<400> SEQUENCE: 1

Ala Glu Val Thr Arg Arg Gly Ser Ala Tyr Tyr Met Tyr Leu Asp Arg
1               5                   10                  15

Asn Asp Ala Gly Glu Ala Ile Ser Phe Pro Thr Thr Leu Gly Met Asn
            20                  25                  30

Lys Cys Tyr Ile Gln Ile Met Asp Leu Gly His Met Cys Asp Ala Thr
        35                  40                  45

Met Ser Tyr Glu Cys Pro Met Leu Asp Glu Gly Val Glu Pro Asp Asp
    50                  55                  60

Val Asp Cys Trp Cys Asn Thr Thr Ser Thr Trp Val Val Tyr Gly Thr
65                  70                  75                  80

Cys His His Lys Lys Gly Glu Ala Arg Arg Ser Arg Arg Ala Val Thr
                85                  90                  95

Leu Pro Ser His Ser Thr Arg Lys Leu Gln Thr Arg Ser Gln Thr Trp
            100                 105                 110

Leu Glu Ser Arg Glu Tyr Thr Lys His Leu Ile Arg Val Glu Asn Trp
        115                 120                 125

Ile Phe Arg Asn Pro Gly Phe Ala Leu Ala Ala Ala Ala Ile Ala Trp
    130                 135                 140

Leu Leu Gly Ser Ser Thr Ser Gln Lys Val Ile Tyr Leu Val Met Ile
145                 150                 155                 160

Leu Leu Ile Ala Pro Ala Tyr Ser Ile Arg Cys Ile Gly Val Ser Asn
                165                 170                 175

Arg Asp Phe Val Glu Gly Met Ser Gly Gly Thr Trp Val Asp Val Val
            180                 185                 190

Leu Glu His Gly Gly Cys Val Thr Val Met Ala Gln Asp Lys Pro Thr
        195                 200                 205

Val Asp Ile Glu Leu Val Thr Thr Thr Val Ser Asn Met Ala Glu Val
    210                 215                 220

Arg Ser Tyr Cys Tyr Glu Ala Ser Ile Ser Asp Met Ala Ser Asp Ser
```

-continued

```
            225                 230                 235                 240
Arg Cys Pro Thr Gln Gly Glu Ala Tyr Leu Asp Lys Gln Ser Asp Thr
                    245                 250                 255
Gln Tyr Val Cys Lys Arg Thr Leu Val Asp Arg Gly Trp Gly Asn Gly
                    260                 265                 270
Cys Gly Leu Phe Gly Lys Gly Ser Leu Val Thr Cys Ala Lys Phe Ala
                    275                 280                 285
Cys Ser Lys Lys Met Thr Gly Lys Ser Ile Gln Pro Glu Asn Leu Glu
            290                 295                 300
Tyr Arg Ile Met Leu Ser Val His Gly Ser Gln His Ser Gly Met Ile
305                 310                 315                 320
Val Asn Asp Thr Gly His Glu Thr Asp Glu Asn Arg Ala Lys Val Glu
                    325                 330                 335
Ile Thr Pro Asn Ser Pro Arg Ala Glu Ala Thr Leu Gly Gly Phe Gly
                    340                 345                 350
Ser Leu Gly Leu Asp Cys Glu Pro Arg Thr Gly Leu Asp Phe Ser Asp
                    355                 360                 365
Leu Tyr Tyr Leu Thr Met Asn Asn Lys His Trp Leu Val His Lys Glu
            370                 375                 380
Trp Phe His Asp Ile Pro Leu Pro Trp His Ala Gly Ala Asp Thr Gly
385                 390                 395                 400
Thr Pro His Trp Asn Asn Lys Glu Ala Leu Val Glu Phe Lys Asp Ala
                    405                 410                 415
His Ala Lys Arg Gln Thr Val Val Leu Gly Ser Gln Glu Gly Ala
                    420                 425                 430
Val His Thr Ala Leu Ala Gly Ala Leu Glu Ala Glu Met Asp Gly Ala
            435                 440                 445
Lys Gly Arg Leu Ser Ser Gly His Leu Lys Cys Arg Leu Lys Met Asp
            450                 455                 460
Lys Leu Arg Leu Lys Gly Val Ser Tyr Ser Leu Cys Thr Ala Ala Phe
465                 470                 475                 480
Thr Phe Thr Lys Ile Pro Ala Glu Thr Leu His Gly Thr Val Thr Val
                    485                 490                 495
Glu Val Gln Tyr Ala Gly Thr Asp Gly Pro Cys Lys Val Pro Ala Gln
                    500                 505                 510
Met Ala Val Asp Met Gln Thr Leu Thr Pro Val Gly Arg Leu Ile Thr
                    515                 520                 525
Ala Asn Pro Val Ile Thr Glu Ser Thr Glu Asn Ser Lys Met Met Leu
            530                 535                 540
Glu Leu Asp Pro Pro Phe Gly Asp Ser Tyr Ile Val Ile Gly Val Gly
545                 550                 555                 560
Glu Lys Lys Ile Thr His His Trp His Arg Ser Gly Ser Thr Ile Gly
                    565                 570                 575
Lys Ala Phe Glu Ala Thr Val Arg Gly Ala Lys Arg Met Ala Val Leu
                    580                 585                 590
Gly Asp Thr Ala Trp Asp Phe Gly Ser Val Gly Gly Ala Leu Asn Ser
                    595                 600                 605
Leu Gly Lys Gly Ile His Gln Ile Phe Gly Ala Ala Phe Lys Ser Leu
            610                 615                 620
Phe Gly Gly Met Ser Trp Phe Ser Gln Ile Leu Ile Gly Thr Leu Leu
625                 630                 635                 640
Met Trp Leu Gly Leu Asn Thr Lys Asn Gly Ser Ile Ser Leu Met Cys
                    645                 650                 655
```

```
Leu Ala Leu Gly Gly Val Leu Ile Phe Leu Ser Thr Ala Val Ser Ala
            660                 665                 670
```

<210> SEQ ID NO 2
<211> LENGTH: 234
<212> TYPE: PRT
<213> ORGANISM: Zika virus
<300> PUBLICATION INFORMATION:
<308> DATABASE ACCESSION NUMBER: GenBank / KU926309.1
<309> DATABASE ENTRY DATE: 2016-03-21
<313> RELEVANT RESIDUES IN SEQ ID NO: (90)..(323)

<400> SEQUENCE: 2

```
Arg Ser Arg Arg Ala Val Thr Leu Pro Ser His Ser Thr Arg Lys Leu
1               5                   10                  15

Gln Thr Arg Ser Gln Thr Trp Leu Glu Ser Arg Glu Tyr Thr Lys His
            20                  25                  30

Leu Ile Arg Val Glu Asn Trp Ile Phe Arg Asn Pro Gly Phe Ala Leu
        35                  40                  45

Ala Ala Ala Ala Ile Ala Trp Leu Leu Gly Ser Ser Thr Ser Gln Lys
    50                  55                  60

Val Ile Tyr Leu Val Met Ile Leu Leu Ile Ala Pro Ala Tyr Ser Ile
65                  70                  75                  80

Arg Cys Ile Gly Val Ser Asn Arg Asp Phe Val Glu Gly Met Ser Gly
                85                  90                  95

Gly Thr Trp Val Asp Val Val Leu Glu His Gly Gly Cys Val Thr Val
            100                 105                 110

Met Ala Gln Asp Lys Pro Thr Val Asp Ile Glu Leu Val Thr Thr Thr
        115                 120                 125

Val Ser Asn Met Ala Glu Val Arg Ser Tyr Cys Tyr Glu Ala Ser Ile
    130                 135                 140

Ser Asp Met Ala Ser Asp Ser Arg Cys Pro Thr Gln Gly Glu Ala Tyr
145                 150                 155                 160

Leu Asp Lys Gln Ser Asp Thr Gln Tyr Val Cys Lys Arg Thr Leu Val
                165                 170                 175

Asp Arg Gly Trp Gly Asn Gly Cys Gly Leu Phe Gly Lys Gly Ser Leu
            180                 185                 190

Val Thr Cys Ala Lys Phe Ala Cys Ser Lys Lys Met Thr Gly Lys Ser
        195                 200                 205

Ile Gln Pro Glu Asn Leu Glu Tyr Arg Ile Met Leu Ser Val His Gly
    210                 215                 220

Ser Gln His Ser Gly Met Ile Val Asn Asp
225                 230
```

<210> SEQ ID NO 3
<211> LENGTH: 3423
<212> TYPE: PRT
<213> ORGANISM: Zika virus
<300> PUBLICATION INFORMATION:
<308> DATABASE ACCESSION NUMBER: GenBank / AMQ48981.1
<309> DATABASE ENTRY DATE: 2016-03-21
<313> RELEVANT RESIDUES IN SEQ ID NO: (1)..(3423)

<400> SEQUENCE: 3

```
Met Lys Asn Pro Lys Lys Lys Ser Gly Gly Phe Arg Ile Val Asn Met
1               5                   10                  15

Leu Lys Arg Gly Val Ala Arg Val Ser Pro Phe Gly Gly Leu Lys Arg
            20                  25                  30
```

-continued

Leu Pro Ala Gly Leu Leu Leu Gly His Gly Pro Ile Arg Met Val Leu
         35                  40                  45

Ala Ile Leu Ala Phe Leu Arg Phe Thr Ala Ile Lys Pro Ser Leu Gly
 50                  55                  60

Leu Ile Asn Arg Trp Gly Ser Val Gly Lys Lys Glu Ala Met Glu Ile
65                  70                  75                  80

Ile Lys Lys Phe Lys Lys Asp Leu Ala Ala Met Leu Arg Ile Ile Asn
                 85                  90                  95

Ala Arg Lys Glu Lys Lys Arg Gly Ala Asp Thr Ser Val Gly Ile
                100                 105                 110

Val Gly Leu Leu Leu Thr Thr Ala Met Ala Ala Glu Val Thr Arg Arg
         115                 120                 125

Gly Ser Ala Tyr Tyr Met Tyr Leu Asp Arg Asn Asp Ala Gly Glu Ala
     130                 135                 140

Ile Ser Phe Pro Thr Thr Leu Gly Met Asn Lys Cys Tyr Ile Gln Ile
145                 150                 155                 160

Met Asp Leu Gly His Met Cys Asp Ala Thr Met Ser Tyr Glu Cys Pro
                165                 170                 175

Met Leu Asp Glu Gly Val Glu Pro Asp Asp Val Asp Cys Trp Cys Asn
        180                 185                 190

Thr Thr Ser Thr Trp Val Val Tyr Gly Thr Cys His His Lys Lys Gly
    195                 200                 205

Glu Ala Arg Arg Ser Arg Arg Ala Val Thr Leu Pro Ser His Ser Thr
    210                 215                 220

Arg Lys Leu Gln Thr Arg Ser Gln Thr Trp Leu Glu Ser Arg Glu Tyr
225                 230                 235                 240

Thr Lys His Leu Ile Arg Val Glu Asn Trp Ile Phe Arg Asn Pro Gly
                245                 250                 255

Phe Ala Leu Ala Ala Ala Ile Ala Trp Leu Leu Gly Ser Ser Thr
        260                 265                 270

Ser Gln Lys Val Ile Tyr Leu Val Met Ile Leu Leu Ile Ala Pro Ala
    275                 280                 285

Tyr Ser Ile Arg Cys Ile Gly Val Ser Asn Arg Asp Phe Val Glu Gly
290                 295                 300

Met Ser Gly Gly Thr Trp Val Asp Val Val Leu Glu His Gly Gly Cys
305                 310                 315                 320

Val Thr Val Met Ala Gln Asp Lys Pro Thr Val Asp Ile Glu Leu Val
                325                 330                 335

Thr Thr Thr Val Ser Asn Met Ala Glu Val Arg Ser Tyr Cys Tyr Glu
            340                 345                 350

Ala Ser Ile Ser Asp Met Ala Ser Asp Ser Arg Cys Pro Thr Gln Gly
        355                 360                 365

Glu Ala Tyr Leu Asp Lys Gln Ser Asp Thr Gln Tyr Val Cys Lys Arg
    370                 375                 380

Thr Leu Val Asp Arg Gly Trp Gly Asn Gly Cys Gly Leu Phe Gly Lys
385                 390                 395                 400

Gly Ser Leu Val Thr Cys Ala Lys Phe Ala Cys Ser Lys Lys Met Thr
                405                 410                 415

Gly Lys Ser Ile Gln Pro Glu Asn Leu Glu Tyr Arg Ile Met Leu Ser
            420                 425                 430

Val His Gly Ser Gln His Ser Gly Met Ile Val Asn Asp Thr Gly His
        435                 440                 445

Glu Thr Asp Glu Asn Arg Ala Lys Val Glu Ile Thr Pro Asn Ser Pro

```
            450                 455                 460
Arg Ala Glu Ala Thr Leu Gly Gly Phe Gly Ser Leu Gly Leu Asp Cys
465                 470                 475                 480

Glu Pro Arg Thr Gly Leu Asp Phe Ser Asp Leu Tyr Tyr Leu Thr Met
                485                 490                 495

Asn Asn Lys His Trp Leu Val His Lys Glu Trp Phe His Asp Ile Pro
                500                 505                 510

Leu Pro Trp His Ala Gly Ala Asp Thr Gly Thr Pro His Trp Asn Asn
            515                 520                 525

Lys Glu Ala Leu Val Glu Phe Lys Asp Ala His Ala Lys Arg Gln Thr
        530                 535                 540

Val Val Val Leu Gly Ser Gln Glu Gly Ala Val His Thr Ala Leu Ala
545                 550                 555                 560

Gly Ala Leu Glu Ala Glu Met Asp Gly Ala Lys Gly Arg Leu Ser Ser
                565                 570                 575

Gly His Leu Lys Cys Arg Leu Lys Met Asp Lys Leu Arg Leu Lys Gly
            580                 585                 590

Val Ser Tyr Ser Leu Cys Thr Ala Ala Phe Thr Phe Thr Lys Ile Pro
        595                 600                 605

Ala Glu Thr Leu His Gly Thr Val Thr Val Glu Val Gln Tyr Ala Gly
    610                 615                 620

Thr Asp Gly Pro Cys Lys Val Pro Ala Gln Met Ala Val Asp Met Gln
625                 630                 635                 640

Thr Leu Thr Pro Val Gly Arg Leu Ile Thr Ala Asn Pro Val Ile Thr
                645                 650                 655

Glu Ser Thr Glu Asn Ser Lys Met Met Leu Glu Leu Asp Pro Pro Phe
            660                 665                 670

Gly Asp Ser Tyr Ile Val Ile Gly Val Gly Glu Lys Lys Ile Thr His
        675                 680                 685

His Trp His Arg Ser Gly Ser Thr Ile Gly Lys Ala Phe Glu Ala Thr
    690                 695                 700

Val Arg Gly Ala Lys Arg Met Ala Val Leu Gly Asp Thr Ala Trp Asp
705                 710                 715                 720

Phe Gly Ser Val Gly Gly Ala Leu Asn Ser Leu Gly Lys Gly Ile His
                725                 730                 735

Gln Ile Phe Gly Ala Ala Phe Lys Ser Leu Phe Gly Gly Met Ser Trp
            740                 745                 750

Phe Ser Gln Ile Leu Ile Gly Thr Leu Leu Met Trp Leu Gly Leu Asn
        755                 760                 765

Thr Lys Asn Gly Ser Ile Ser Leu Met Cys Leu Ala Leu Gly Gly Val
    770                 775                 780

Leu Ile Phe Leu Ser Thr Ala Val Ser Ala Asp Val Gly Cys Ser Val
785                 790                 795                 800

Asp Phe Ser Lys Lys Glu Thr Arg Cys Gly Thr Gly Val Phe Val Tyr
                805                 810                 815

Asn Asp Val Glu Ala Trp Arg Asp Arg Tyr Lys Tyr His Pro Asp Ser
            820                 825                 830

Pro Arg Arg Leu Ala Ala Ala Val Lys Gln Ala Trp Glu Asp Gly Ile
        835                 840                 845

Cys Gly Ile Ser Ser Val Ser Arg Met Glu Asn Ile Met Trp Arg Ser
    850                 855                 860

Val Glu Gly Glu Leu Asn Ala Ile Leu Glu Glu Asn Gly Val Gln Leu
865                 870                 875                 880
```

```
Thr Val Val Val Gly Ser Val Lys Asn Pro Met Trp Arg Gly Pro Gln
            885                 890                 895

Arg Leu Pro Val Pro Val Asn Glu Leu Pro His Gly Trp Lys Ala Trp
            900                 905                 910

Gly Lys Ser Tyr Phe Val Arg Ala Ala Lys Thr Asn Asn Ser Phe Val
            915                 920                 925

Val Asp Gly Asp Thr Leu Lys Glu Cys Pro Leu Lys His Arg Ala Trp
930                 935                 940

Asn Ser Phe Leu Val Glu Asp His Gly Phe Gly Val Phe His Thr Ser
945                 950                 955                 960

Val Trp Leu Lys Val Arg Glu Asp Tyr Ser Leu Glu Cys Asp Pro Ala
            965                 970                 975

Val Ile Gly Thr Ala Val Lys Gly Lys Glu Ala Val His Ser Asp Leu
            980                 985                 990

Gly Tyr Trp Ile Glu Ser Glu Lys Asn Asp Thr Trp Arg Leu Lys Arg
            995                 1000                1005

Ala His Leu Ile Glu Met Lys Thr Cys Glu Trp Pro Lys Ser His
        1010                1015                1020

Thr Leu Trp Thr Asp Gly Ile Glu Glu Ser Asp Leu Ile Ile Pro
        1025                1030                1035

Lys Ser Leu Ala Gly Pro Leu Ser His His Asn Thr Arg Glu Gly
        1040                1045                1050

Tyr Arg Thr Gln Met Lys Gly Pro Trp His Ser Glu Glu Leu Glu
        1055                1060                1065

Ile Arg Phe Glu Glu Cys Pro Gly Thr Lys Val His Val Glu Glu
        1070                1075                1080

Thr Cys Gly Thr Arg Gly Pro Ser Leu Arg Ser Thr Thr Ala Ser
        1085                1090                1095

Gly Arg Val Ile Glu Glu Trp Cys Cys Arg Glu Cys Thr Met Pro
        1100                1105                1110

Pro Leu Ser Phe Arg Ala Lys Asp Gly Cys Trp Tyr Gly Met Glu
        1115                1120                1125

Ile Arg Pro Arg Lys Glu Pro Glu Ser Asn Leu Val Arg Ser Met
        1130                1135                1140

Val Thr Ala Gly Ser Thr Asp His Met Asp His Phe Ser Leu Gly
        1145                1150                1155

Val Leu Val Ile Leu Leu Met Val Gln Glu Gly Leu Lys Lys Arg
        1160                1165                1170

Met Thr Thr Lys Ile Ile Ile Ser Thr Ser Met Ala Val Leu Val
        1175                1180                1185

Ala Met Ile Leu Gly Gly Phe Ser Met Ser Asp Leu Ala Lys Leu
        1190                1195                1200

Ala Ile Leu Met Gly Ala Thr Phe Ala Glu Met Asn Thr Gly Gly
        1205                1210                1215

Asp Val Ala His Leu Ala Leu Ile Ala Ala Phe Lys Val Arg Pro
        1220                1225                1230

Ala Leu Leu Val Ser Phe Ile Phe Arg Ala Asn Trp Thr Pro Arg
        1235                1240                1245

Glu Ser Met Leu Leu Ala Leu Ala Ser Cys Leu Leu Gln Thr Ala
        1250                1255                1260

Ile Ser Ala Leu Glu Gly Asp Leu Met Val Leu Ile Asn Gly Phe
        1265                1270                1275
```

-continued

Ala Leu Ala Trp Leu Ala Ile Arg Ala Met Val Val Pro Arg Thr
    1280            1285            1290

Asp Asn Ile Thr Leu Ala Ile Leu Ala Ala Leu Thr Pro Leu Ala
    1295            1300            1305

Arg Gly Thr Leu Leu Val Ala Trp Arg Ala Gly Leu Ala Thr Cys
    1310            1315            1320

Gly Gly Phe Met Leu Leu Ser Leu Lys Gly Lys Gly Ser Val Lys
    1325            1330            1335

Lys Asn Leu Pro Phe Val Met Ala Leu Gly Leu Thr Ala Val Arg
    1340            1345            1350

Leu Val Asp Pro Ile Asn Val Val Gly Leu Leu Leu Thr Arg
    1355            1360            1365

Ser Gly Lys Arg Ser Trp Pro Pro Ser Glu Val Leu Thr Ala Val
    1370            1375            1380

Gly Leu Ile Cys Ala Leu Ala Gly Gly Phe Ala Lys Ala Asp Ile
    1385            1390            1395

Glu Met Ala Gly Pro Ile Ala Ala Val Gly Leu Leu Ile Val Ser
    1400            1405            1410

Tyr Val Val Ser Gly Lys Ser Val Asp Met Tyr Ile Glu Arg Ala
    1415            1420            1425

Gly Asp Ile Thr Trp Glu Lys Asp Ala Glu Val Thr Gly Asn Ser
    1430            1435            1440

Pro Arg Leu Asp Val Ala Leu Asp Glu Ser Gly Asp Phe Ser Leu
    1445            1450            1455

Val Glu Asp Asp Gly Pro Pro Met Arg Glu Ile Ile Leu Lys Val
    1460            1465            1470

Val Leu Met Thr Ile Cys Gly Met Asn Pro Ile Ala Ile Pro Phe
    1475            1480            1485

Ala Ala Gly Ala Trp Tyr Val Tyr Val Lys Thr Gly Lys Arg Ser
    1490            1495            1500

Gly Ala Leu Trp Asp Val Pro Ala Pro Lys Glu Val Lys Lys Gly
    1505            1510            1515

Glu Thr Thr Asp Gly Val Tyr Arg Val Met Thr Arg Arg Leu Leu
    1520            1525            1530

Gly Ser Thr Gln Val Gly Val Gly Val Met Gln Glu Gly Val Phe
    1535            1540            1545

His Thr Met Trp His Val Thr Lys Gly Ser Ala Leu Arg Ser Gly
    1550            1555            1560

Glu Gly Arg Leu Asp Pro Tyr Trp Gly Asp Val Lys Gln Asp Leu
    1565            1570            1575

Val Ser Tyr Cys Gly Pro Trp Lys Leu Asp Ala Ala Trp Asp Gly
    1580            1585            1590

His Ser Glu Val Gln Leu Leu Ala Val Pro Pro Gly Glu Arg Ala
    1595            1600            1605

Arg Asn Ile Gln Thr Leu Pro Gly Ile Phe Lys Thr Lys Asp Gly
    1610            1615            1620

Asp Ile Gly Ala Val Ala Leu Asp Tyr Pro Ala Gly Thr Ser Gly
    1625            1630            1635

Ser Pro Ile Leu Asp Lys Cys Gly Arg Val Ile Gly Leu Tyr Gly
    1640            1645            1650

Asn Gly Val Val Ile Lys Asn Gly Ser Tyr Val Ser Ala Ile Thr
    1655            1660            1665

Gln Gly Arg Arg Glu Glu Glu Thr Pro Val Glu Cys Phe Glu Pro

-continued

```
            1670                1675                1680
Ser Met Leu Lys Lys Gln Leu Thr Val Leu Asp Leu His Pro
    1685                1690                1695

Gly Ala Gly Lys Thr Arg Arg Val Leu Pro Glu Ile Val Arg Glu
    1700                1705                1710

Ala Ile Lys Thr Arg Leu Arg Thr Val Ile Leu Ala Pro Thr Arg
    1715                1720                1725

Val Val Ala Ala Glu Met Glu Glu Ala Leu Arg Gly Leu Pro Val
    1730                1735                1740

Arg Tyr Met Thr Thr Ala Val Asn Val Thr His Ser Gly Thr Glu
    1745                1750                1755

Ile Val Asp Leu Met Cys His Ala Thr Phe Thr Ser Arg Leu Leu
    1760                1765                1770

Gln Pro Ile Arg Val Pro Asn Tyr Asn Leu Tyr Ile Met Asp Glu
    1775                1780                1785

Ala His Phe Thr Asp Pro Ser Ser Ile Ala Ala Arg Gly Tyr Ile
    1790                1795                1800

Ser Thr Arg Val Glu Met Gly Glu Ala Ala Ile Phe Met Thr
    1805                1810                1815

Ala Thr Pro Pro Gly Thr Arg Asp Ala Phe Pro Asp Ser Asn Ser
    1820                1825                1830

Pro Ile Met Asp Thr Glu Val Glu Val Pro Glu Arg Ala Trp Ser
    1835                1840                1845

Ser Gly Phe Asp Trp Val Thr Asp His Ser Gly Lys Thr Val Trp
    1850                1855                1860

Phe Val Pro Ser Val Arg Asn Gly Asn Glu Ile Ala Ala Cys Leu
    1865                1870                1875

Thr Lys Ala Gly Lys Arg Val Ile Gln Leu Ser Arg Lys Thr Phe
    1880                1885                1890

Glu Thr Glu Phe Gln Lys Thr Lys His Gln Glu Trp Asp Phe Val
    1895                1900                1905

Val Thr Thr Asp Ile Ser Glu Met Gly Ala Asn Phe Lys Ala Asp
    1910                1915                1920

Arg Val Ile Asp Ser Arg Arg Cys Leu Lys Pro Val Ile Leu Asp
    1925                1930                1935

Gly Glu Arg Val Ile Leu Ala Gly Pro Met Pro Val Thr His Ala
    1940                1945                1950

Ser Ala Ala Gln Arg Arg Gly Arg Ile Gly Arg Asn Pro Asn Lys
    1955                1960                1965

Pro Gly Asp Glu Tyr Leu Tyr Gly Gly Gly Cys Ala Glu Thr Asp
    1970                1975                1980

Glu Asp His Ala His Trp Leu Glu Ala Arg Met Leu Leu Asp Asn
    1985                1990                1995

Ile Tyr Leu Gln Asp Gly Leu Ile Ala Ser Leu Tyr Arg Pro Glu
    2000                2005                2010

Ala Asp Lys Val Ala Ala Ile Glu Gly Glu Phe Lys Leu Arg Thr
    2015                2020                2025

Glu Gln Arg Lys Thr Phe Val Glu Leu Met Arg Arg Gly Asp Leu
    2030                2035                2040

Pro Val Trp Leu Ala Tyr Gln Val Ala Ser Ala Gly Ile Thr Tyr
    2045                2050                2055

Thr Asp Arg Arg Trp Cys Phe Asp Gly Thr Thr Asn Asn Thr Ile
    2060                2065                2070
```

-continued

```
Met Glu Asp Ser Val Pro Ala Glu Val Trp Thr Arg His Gly Glu
2075                2080                2085

Lys Arg Val Leu Lys Pro Arg Trp Met Asp Arg Val Cys Ser
2090                2095                2100

Asp His Ala Ala Leu Lys Ser Phe Lys Glu Phe Ala Ala Gly Lys
2105                2110                2115

Arg Gly Ala Ala Phe Gly Val Met Glu Ala Leu Gly Thr Leu Pro
2120                2125                2130

Gly His Met Thr Glu Arg Phe Gln Glu Ala Ile Asp Asn Leu Ala
2135                2140                2145

Val Leu Met Arg Ala Glu Thr Gly Ser Arg Pro Tyr Lys Ala Ala
2150                2155                2160

Ala Ala Gln Leu Pro Glu Thr Leu Glu Thr Ile Met Leu Leu Gly
2165                2170                2175

Leu Leu Gly Thr Val Ser Leu Gly Ile Phe Phe Val Leu Met Arg
2180                2185                2190

Asn Lys Gly Ile Gly Lys Met Gly Phe Gly Met Val Thr Leu Gly
2195                2200                2205

Ala Ser Ala Trp Leu Met Trp Leu Ser Glu Ile Glu Pro Ala Arg
2210                2215                2220

Ile Ala Cys Val Leu Ile Val Val Phe Leu Leu Leu Val Val Leu
2225                2230                2235

Ile Pro Glu Pro Glu Lys Gln Arg Ser Pro Gln Asp Asn Gln Met
2240                2245                2250

Ala Ile Ile Ile Met Val Ala Val Gly Leu Leu Gly Leu Ile Thr
2255                2260                2265

Ala Asn Glu Leu Gly Trp Leu Glu Arg Thr Lys Ser Asp Leu Ser
2270                2275                2280

His Leu Met Gly Arg Arg Glu Glu Gly Ala Thr Ile Gly Phe Ser
2285                2290                2295

Met Asp Ile Asp Leu Arg Pro Ala Ser Ala Trp Ala Ile Tyr Ala
2300                2305                2310

Ala Leu Thr Thr Phe Ile Thr Pro Ala Val Gln His Ala Val Thr
2315                2320                2325

Thr Ser Tyr Asn Asn Tyr Ser Leu Met Ala Met Ala Thr Gln Ala
2330                2335                2340

Gly Val Leu Phe Gly Met Gly Lys Gly Met Pro Phe Tyr Ala Trp
2345                2350                2355

Asp Phe Gly Val Pro Leu Leu Met Ile Gly Cys Tyr Ser Gln Leu
2360                2365                2370

Thr Pro Leu Thr Leu Ile Val Ala Ile Ile Leu Leu Val Ala His
2375                2380                2385

Tyr Met Tyr Leu Ile Pro Gly Leu Gln Ala Ala Ala Arg Ala
2390                2395                2400

Ala Gln Lys Arg Thr Ala Ala Gly Ile Met Lys Asn Pro Val Val
2405                2410                2415

Asp Gly Ile Val Val Thr Asp Ile Asp Thr Met Thr Ile Asp Pro
2420                2425                2430

Gln Val Glu Lys Lys Met Gly Gln Val Leu Leu Ile Ala Val Ala
2435                2440                2445

Val Ser Ser Ala Ile Leu Ser Arg Thr Ala Trp Gly Trp Gly Glu
2450                2455                2460
```

```
Ala Gly Ala Leu Ile Thr Ala Ala Thr Ser Thr Leu Trp Glu Gly
    2465                2470                2475

Ser Pro Asn Lys Tyr Trp Asn Ser Ser Thr Ala Thr Ser Leu Cys
    2480                2485                2490

Asn Ile Phe Arg Gly Ser Tyr Leu Ala Gly Ala Ser Leu Ile Tyr
    2495                2500                2505

Thr Val Thr Arg Asn Ala Gly Leu Val Lys Arg Arg Gly Gly Gly
    2510                2515                2520

Thr Gly Glu Thr Leu Gly Glu Lys Trp Lys Ala Arg Leu Asn Gln
    2525                2530                2535

Met Ser Ala Leu Glu Phe Tyr Ser Tyr Lys Lys Ser Gly Ile Thr
    2540                2545                2550

Glu Val Cys Arg Glu Glu Ala Arg Arg Ala Leu Lys Asp Gly Val
    2555                2560                2565

Ala Thr Gly Gly His Ala Val Ser Arg Gly Ser Ala Lys Leu Arg
    2570                2575                2580

Trp Leu Val Glu Arg Gly Tyr Leu Gln Pro Tyr Gly Lys Val Ile
    2585                2590                2595

Asp Leu Gly Cys Gly Arg Gly Gly Trp Ser Tyr Tyr Ala Ala Thr
    2600                2605                2610

Ile Arg Lys Val Gln Glu Val Lys Gly Tyr Thr Lys Gly Gly Pro
    2615                2620                2625

Gly His Glu Glu Pro Val Leu Val Gln Ser Tyr Gly Trp Asn Ile
    2630                2635                2640

Val Arg Leu Lys Ser Gly Val Asp Val Phe His Met Ala Ala Glu
    2645                2650                2655

Pro Cys Asp Thr Leu Leu Cys Asp Ile Gly Glu Ser Ser Ser Ser
    2660                2665                2670

Pro Glu Val Glu Glu Ala Arg Thr Leu Arg Val Leu Ser Met Val
    2675                2680                2685

Gly Asp Trp Leu Glu Lys Arg Pro Gly Ala Phe Cys Ile Lys Val
    2690                2695                2700

Leu Cys Pro Tyr Thr Ser Thr Met Met Glu Thr Leu Glu Arg Leu
    2705                2710                2715

Gln Arg Arg Tyr Gly Gly Gly Leu Val Arg Val Pro Leu Ser Arg
    2720                2725                2730

Asn Ser Thr His Glu Met Tyr Trp Val Ser Gly Ala Lys Ser Asn
    2735                2740                2745

Thr Ile Lys Ser Val Ser Thr Thr Ser Gln Leu Leu Leu Gly Arg
    2750                2755                2760

Met Asp Gly Pro Arg Arg Pro Val Lys Tyr Glu Glu Asp Val Asn
    2765                2770                2775

Leu Gly Ser Gly Thr Arg Ala Val Val Ser Cys Ala Glu Ala Pro
    2780                2785                2790

Asn Met Lys Ile Ile Gly Asn Arg Ile Glu Arg Ile Arg Ser Glu
    2795                2800                2805

His Ala Glu Thr Trp Phe Phe Asp Glu Asn His Pro Tyr Arg Thr
    2810                2815                2820

Trp Ala Tyr His Gly Ser Tyr Glu Ala Pro Thr Gln Gly Ser Ala
    2825                2830                2835

Ser Ser Leu Ile Asn Gly Val Val Arg Leu Leu Ser Lys Pro Trp
    2840                2845                2850

Asp Val Val Thr Gly Val Thr Gly Ile Ala Met Thr Asp Thr Thr
```

```
             2855                2860                2865
Pro Tyr Gly Gln Gln Arg Val Phe Lys Glu Lys Val Asp Thr Arg
            2870                2875                2880
Val Pro Asp Pro Gln Glu Gly Thr Arg Gln Val Met Ser Met Val
            2885                2890                2895
Ser Ser Trp Leu Trp Lys Glu Leu Gly Lys His Lys Arg Pro Arg
            2900                2905                2910
Val Cys Thr Lys Glu Glu Phe Ile Asn Lys Val Arg Ser Asn Ala
            2915                2920                2925
Ala Leu Gly Ala Ile Phe Glu Glu Lys Glu Trp Lys Thr Ala
            2930                2935                2940
Val Glu Ala Val Asn Asp Pro Arg Phe Trp Ala Leu Val Asp Lys
            2945                2950                2955
Glu Arg Glu His His Leu Arg Gly Glu Cys Gln Ser Cys Val Tyr
            2960                2965                2970
Asn Met Met Gly Lys Arg Glu Lys Lys Gln Gly Glu Phe Gly Lys
            2975                2980                2985
Ala Lys Gly Ser Arg Ala Ile Trp Tyr Met Trp Leu Gly Ala Arg
            2990                2995                3000
Phe Leu Glu Phe Glu Ala Leu Gly Phe Leu Asn Glu Asp His Trp
            3005                3010                3015
Met Gly Arg Glu Asn Ser Gly Gly Gly Val Glu Gly Leu Gly Leu
            3020                3025                3030
Gln Arg Leu Gly Tyr Val Leu Glu Glu Met Ser Arg Ile Pro Gly
            3035                3040                3045
Gly Arg Met Tyr Ala Asp Asp Thr Ala Gly Trp Asp Thr Arg Ile
            3050                3055                3060
Ser Arg Phe Asp Leu Glu Asn Glu Ala Leu Ile Thr Asn Gln Met
            3065                3070                3075
Glu Lys Gly His Arg Ala Leu Ala Leu Ala Ile Ile Lys Tyr Thr
            3080                3085                3090
Tyr Gln Asn Lys Val Val Lys Val Leu Arg Pro Ala Glu Lys Gly
            3095                3100                3105
Lys Thr Val Met Asp Ile Ile Ser Arg Gln Asp Gln Arg Gly Ser
            3110                3115                3120
Gly Gln Val Val Thr Tyr Ala Leu Asn Thr Phe Thr Asn Leu Val
            3125                3130                3135
Val Gln Leu Ile Arg Asn Met Glu Ala Glu Glu Val Leu Glu Met
            3140                3145                3150
Gln Asp Leu Trp Leu Leu Arg Arg Ser Glu Lys Val Thr Asn Trp
            3155                3160                3165
Leu Gln Ser Asn Gly Trp Asp Arg Leu Lys Arg Met Ala Val Ser
            3170                3175                3180
Gly Asp Asp Cys Val Val Lys Pro Ile Asp Asp Arg Phe Ala His
            3185                3190                3195
Ala Leu Arg Phe Leu Asn Asp Met Gly Lys Val Arg Lys Asp Thr
            3200                3205                3210
Gln Glu Trp Lys Pro Ser Thr Gly Trp Asp Asn Trp Glu Glu Val
            3215                3220                3225
Pro Phe Cys Ser His His Phe Asn Lys Leu His Leu Lys Asp Gly
            3230                3235                3240
Arg Ser Ile Val Val Pro Cys Arg His Gln Asp Glu Leu Ile Gly
            3245                3250                3255
```

```
Arg Ala Arg Val Ser Pro Gly Ala Gly Trp Ser Ile Arg Glu Thr
3260                 3265                 3270

Ala Cys Leu Ala Lys Ser Tyr Ala Gln Met Trp Gln Leu Leu Tyr
3275                 3280                 3285

Phe His Arg Arg Asp Leu Arg Leu Met Ala Asn Ala Ile Cys Ser
3290                 3295                 3300

Ser Val Pro Val Asp Trp Val Pro Thr Gly Arg Thr Thr Trp Ser
3305                 3310                 3315

Ile His Gly Lys Gly Glu Trp Met Thr Thr Glu Asp Met Leu Val
3320                 3325                 3330

Val Trp Asn Arg Val Trp Ile Glu Glu Asn Asp His Met Glu Asp
3335                 3340                 3345

Lys Thr Pro Val Thr Lys Trp Thr Asp Ile Pro Tyr Leu Gly Lys
3350                 3355                 3360

Arg Glu Asp Leu Trp Cys Gly Ser Leu Ile Gly His Arg Pro Arg
3365                 3370                 3375

Thr Thr Trp Ala Glu Asn Ile Lys Asn Thr Val Asn Met Val Arg
3380                 3385                 3390

Arg Ile Ile Gly Asp Glu Glu Lys Tyr Met Asp Tyr Leu Ser Thr
3395                 3400                 3405

Gln Val Arg Tyr Leu Gly Glu Glu Gly Ser Thr Pro Gly Val Leu
3410                 3415                 3420

<210> SEQ ID NO 4
<211> LENGTH: 10795
<212> TYPE: DNA
<213> ORGANISM: Zika virus
<300> PUBLICATION INFORMATION:
<308> DATABASE ACCESSION NUMBER: GenBank / KU926309.1
<309> DATABASE ENTRY DATE: 2016-03-21
<313> RELEVANT RESIDUES IN SEQ ID NO: (1)..(10795)

<400> SEQUENCE: 4
gatctgtgtg aatcagactg cgacagttcg agtttgaagc gaaagctagc aacagtatca      60
acaggtttta ttttggattt ggaaacgaga gtttctggtc atgaaaaacc caaaaagaa     120 atccggagga ttccggattg tcaatatgct aaaacgcgga gtagcccgtg tgagcccctt     180
tgggggcttg aagaggctgc agccggact tctgctgggt catgggccca tcaggatggt     240
cttggcgatt ctagcctttt tgagattcac ggcaatcaag ccatcactgg gtctcatcaa     300
tagatgggga tcagtgggga aaaagaggc tatggaaata ataaagaagt tcaagaaaga     360
tctggctgcc atgctgagaa taatcaatgc taggaaggag aagaagagac gaggcgcaga     420
tactagtgtc ggaattgttg gcctcctgct gaccacagct atggcagcgg aggtcactag     480
acgtgggagt gcatactaca tgtacttgga cagaaacgat gctggggagg ccatatcttt     540
tccaaccaca ttggggatga ataagtgtta tatacagatc atggatcttg acacatgtg     600 tgatgccacc atgagctatg aatgccctat gctggatgag ggggtggaac cagatgacgt     660
cgattgttgg tgcaacacga cgtcaacttg ggttgtgtac ggaacctgcc atcacaaaaa     720
aggtgaagca cggagatcta aagagctgt gacgctcccc tcccattcca ctaggaagct     780
gcaaacgcgg tcgcaaacct ggttggaatc gagagaatac acaaagcact tgattagagt     840
cgaaaattgg atattcagga acctggctt cgcgttagca gcagctgcca tcgcttggct     900
tttgggaagc tcaacgagcc aaaaagtcat atacttggtc atgatactgc tgattgcccc     960
ggcatacagc atcaggtgca taggagtcag caatagggac tttgtggaag gtatgtcagg    1020
```

```
tgggacttgg gttgatgttg tcttggaaca tggaggttgt gtcaccgtaa tggcacagga    1080
taaaccgact gtcgacatag agctggttac aacaacagtc agcaacatgg cggaggtaag    1140
atcctactgc tatgaggcat caatatcaga catggcttcg acagccgct gcccaacaca     1200 aggtgaagcc taccttgaca agcaatcaga cactcaatat gtctgcaaaa gaacgttagt    1260
ggacagaggc tggggaaatg gatgtggact ttttggcaaa gggagcctgg tgacatgcgc    1320
taagtttgca tgctccaaga aaatgaccgg gaagagcatc cagccagaga atctggagta    1380
ccggataatg ctgtcagttc atggctccca gcacagtggg atgatcgtta atgacacagg    1440
acatgaaact gatgagaata gagcgaaggt tgagataacg cccaattcac caagagccga    1500
agccaccctg gggggttttg gaagcctagg acttgattgt gaaccgagga caggccttga    1560
cttttcagat ttgtattact tgactatgaa taacaagcac tggttggttc acaaggagtg    1620
gttccacgac attccattgc cttggcacgc tggggcagac accggaactc cacactggaa    1680
caacaaagaa gcactggtag agttcaagga cgcacatgcc aaaaggcaaa ctgtcgtggt    1740
tctagggagt caagaaggag cagttcacac ggcccttgct ggagctctgg aggctgagat    1800
ggatggtgca aagggaaggc tgtcctctgg ccacttgaaa tgtcgcctga aaatggataa    1860
acttagattg aagggcgtgt catactcctt gtgtaccgca gcgttcacat tcaccaagat    1920
cccggctgaa acactgcacg ggacagtcac agtggaggta cagtacgcag ggacagatgg    1980
accttgcaag gttccagctc agatggcggt ggacatgcaa actctgaccc cagttgggag    2040
gttgataacc gctaacccg taatcactga aagcactgag aactctaaga tgatgctgga     2100
acttgatcca ccatttgggg actcttacat tgtcatagga gtcggggaga agaagatcac    2160
ccaccactgg cacaggagtg gcagcaccat tggaaaagca tttgaagcca ctgtgagagg    2220
tgccaagaga atggcagtct gggagacac agcctgggac tttggatcag ttggaggcgc    2280
tctcaactca ttgggcaagg gcatccatca aattttttgga gcagctttca atcattgtt    2340 tggaggaatg tcctggttct cacaaattct cattggaacg ttgctgatgt ggttgggcct    2400
gaacacaaag aatggatcta tttccttat gtgcttggcc ttaggggag tgttgatctt      2460 cttatccaca gccgtctctg ctgatgtggg gtgctcggtg gacttctcaa agaaggagac    2520
gagatgcggt acagggtgt tcgtctataa cgacgttgaa gcctggaggg acaggtacaa     2580
gtaccatcct gactcccccc gtagattggc agcagcagtc aagcaagcct gggaagatgg    2640
tatctgcggg atctcctctg tttcaagaat ggaaaacatc atgtggagat cagtagaagg    2700
ggagctcaac gcaatcctgg aagagaatgg agttcaactg acggtcgttg tgggatcggt    2760
aaaaaacccc atgtggagag gtccacagag attgcccgtg cctgtgaacg agctgccca     2820 cggctggaag gcttggggga atcgtactt cgtcagagca gcaaagacaa ataacagctt     2880
tgtcgtggat ggtgacacac tgaaggaatg cccactcaaa catagagcat ggaacagctt    2940
tcttgtggag gatcatgggt tcggggtatt tcacactagt gtctggctca aggttagaga    3000
agattattca ttagagtgtg atccagccgt tattggaaca gctgttaagg gaaaggaggc    3060
tgtacacagt gatctaggct actggattga gagtgagaag aatgacacat ggaggctgaa    3120
gagggcccat ctgatcgaga tgaaaacatg tgaatggcca aagtcccaca cattgtggac    3180
agatggaata gaagagagtg atctgatcat acccaagtct ttagctgggc cactcagcca    3240
tcacaatacc agagagggct acaggaccca aatgaagggg ccatggcaca gtgaagagct    3300
tgaaattcgg tttgaggaat gcccaggcac taaggtccac gtggaggaaa catgtggaac    3360
```

-continued

```
aagaggacca tctctgagat caaccactgc aagcggaagg gtgatcgagg aatggtgctg    3420
cagggagtgc acaatgcccc cactgtcgtt ccgggctaaa gatggctgtt ggtatggaat    3480
ggagataagg cccaggaaag aaccagaaag caacttagta aggtcaatgg tgactgcagg    3540
atcaactgat cacatggatc acttctccct tggagtgctt gtgattctgc tcatggtgca    3600
ggaagggctg aagaagagaa tgaccacaaa gatcatcata agcacatcaa tggcagtgct    3660
ggtagctatg atcctgggag gattttcaat gagtgacctg gctaagcttg caattttgat    3720
gggtgccacc ttcgcggaaa tgaacactgg aggagatgta gctcatctgg cgctgatagc    3780
ggcattcaaa gtcagaccag cgttgctggt atctttcatc ttcagagcta attggacacc    3840
ccgtgaaagc atgctgctgg ccttggcctc gtgtcttttg caaactgcga tctccgcctt    3900
ggaaggcgac ctgatggttc tcatcaatgg ttttgctttg gcctggttgg caatacgagc    3960
gatggttgtt ccacgcactg ataacatcac cttggcaatc ctggctgctc tgacaccact    4020
ggcccggggc acactgcttg tggcgtggag agcaggcctt gctacttgcg gggggtttat    4080
gctcctctct ctgaagggaa aaggcagtgt gaagaagaac ttaccatttg tcatggccct    4140
gggactaacc gctgtgaggc tggtcgaccc catcaacgtg gtgggactgc tgttgctcac    4200
aaggagtggg aagcggagct ggccccctag cgaagtactc acagctgttg gcctgatatg    4260
cgcattggct ggagggttcg ccaaggcaga tatagagatg gctgggccca tagccgcggt    4320
cggtctgcta attgtcagtt acgtggtctc aggaaagagt gtggacatgt acattgaaag    4380
agcaggtgac atcacatggg aaaaagatgc ggaagtcact ggaaacagtc cccggctcga    4440
tgtggcgcta gatgagagtg gtgatttctc cctggtggag gatgacggtc ccccatgag    4500 agagatcata ctcaaggtgg tcctgatgac catctgtggc atgaacccaa tagccatacc    4560
ttttgcagct ggagcgtggt acgtatacgt gaagactgga aaaaggagtg gtgctctatg    4620
ggatgtgcct gctcccaagg aagtaaaaaa gggggagacc acagatggag tgtacagagt    4680
aatgactcgt agactgctgg gttcaacaca agttggagtg ggagttatgc aagagggggt    4740 cttcacact atgtggcacg tcacaaaagg atccgcactg agaagcggtg aagggagact    4800
tgatccatac tggggagatg tcaagcagga tctggtgtca tactgtggtc catggaagct    4860
agatgccgcc tgggacgggc acagcgaggt gcagctcttg gccgtgcccc ccggagagag    4920
agcgaggaac atccagactc tgcccggaat atttaagaca aaggatgggg acattggagc    4980
ggttgcgctg gattacccag caggaacttc aggatctcca atcctagaca gtgtgggag    5040 agtgatagga ctttatggca atggggtcgt gatcaaaaat gggagttatg ttagtgccat    5100
cacccaaggg aggagggagg aagagactcc tgttgagtgc ttcgagcctt cgatgctgaa    5160
gaagaagcag ctaactgtct tagacttgca tcctggagct gggaaaacca ggagagttct    5220
tcctgaaata gtccgtgaag ccataaaaac aagactccgt actgtgatct tagctccaac    5280
cagggttgtc gctgctgaaa tggaggaggc ccttagaggg cttccagtgc gttatatgac    5340
aacagcagtc aatgtcaccc actctggaac agaaatcgtc gacttaatgt gccatgccac    5400
cttcacttca cgtctactac agccaatcag agtccccaac tataatctgt atattatgga    5460
tgaggcccac ttcacagatc cctcaagtat agcagcaaga ggatacattt caacaagggt    5520
tgagatgggc gaggcggctg ccatcttcat gaccgccacg ccaccaggaa cccgtgacgc    5580
atttccggac tccaactcac caattatgga caccgaagtg gaagtccag agagagcctg    5640 gagctcaggc tttgattggg tgacggatca ttctggaaaa acagtttggt tgttccaag    5700 cgtgaggaac ggcaatgaga tcgcagcttg tctgacaaag gctggaaaac gggtcataca    5760
```

```
gctcagcaga aagactttg agacagagtt ccagaaaaca aaacatcaag agtgggactt    5820
tgtcgtgaca actgacattt cagagatggg cgccaacttt aaagctgacc gtgtcataga    5880
ttccaggaga tgcctaaagc cggtcatact tgatggcgag agagtcattc tggctggacc    5940
catgcctgtc acacatgcca gcgctgccca gaggaggggg cgcataggca ggaatcccaa    6000
caaacctgga gatgagtatc tgtatggagg tgggtgcgca gagactgacg aagaccatgc    6060
acactggctt gaagcaagaa tgctccttga caatatttac ctccaagatg gcctcatagc    6120
ctcgctctat cgacctgagg ccgacaaagt agcagccatt gagggagagt tcaagcttag    6180
gacggagcaa aggaagacct tgtggaact catgagaaga ggagatcttc ctgtttggct    6240
ggcctatcag gttgcatctg ccggaataac ctacacagat agaagatggt gctttgatgg    6300
cacgaccaac aacaccataa tggaagacag tgtgccggca gaggtgtgga ccagacacgg    6360
agagaaaaga gtgctcaaac cgaggtggat ggacgccaga gtttgttcag atcatgcggc    6420
cctgaagtca ttcaaggagt ttgccgctgg gaaaagagga gcggcttttg gagtgatgga    6480
agccctggga acactgccag gacacatgac agagagattc caggaagcca ttgacaacct    6540
cgctgtgctc atgcgggcag agactggaag caggccttac aaagccgcgg cggcccaatt    6600
gccggagacc ctagagacca ttatgctttt ggggttgttg gaacagtct cgctgggaat    6660 ctttttcgtc ttgatgagga caagggcat agggaagatg ggctttggaa tggtgactct    6720 tgggggccagc gcatggctca tgtggctctc ggaaattgag ccagccagaa ttgcatgtgt    6780
cctcattgtt gtgttcctat tgctggtggt gctcatacct gagccagaaa agcaaagatc    6840
tccccaggac aaccaaatgg caatcatcat catggtagca gtaggtcttc tgggcttgat    6900
taccgccaat gaactcggat ggttggagag aacaaagagt gacctaagcc atctaatggg    6960
aaggagagag gaggggcaa ccataggatt ctcaatggac attgacctgc ggccagcctc    7020
agcttgggcc atctatgctg ccttgacaac tttcattacc ccagccgtcc aacatgcagt    7080
gaccacttca tacaacaact actccttaat ggcgatggcc acgcaagctg gagtgttgtt    7140
tggtatgggc aaagggatgc cattctacgc atgggacttt ggagtcccgc tgctaatgat    7200
aggttgctac tcacaattaa caccctgac cctaatagtg gccatcattt tgctcgtggc    7260
gcactacatg tacttgatcc cagggctgca ggcagcagct gcgcgtgctg cccagaagag    7320
aacggcagct ggcatcatga agaaccctgt tgtggatgga atagtggtga ctgacattga    7380
cacaatgaca attgaccccc aagtggagaa aaagatggga caggtgctac tcatagcagt    7440 agcctgtctcc agcgccatac tgtcgcggac cgcctggggg tgggggagg ctgggcccct    7500 gatcacagcc gcaacttcca ctttgtggga aggctctccg aacaagtact ggaactcctc    7560
tacagccact tcactgtgta acattttag gggaagttac ttggctggag cttctctaat    7620
ctacacagta acaagaaacg ctggcttggt caagagacgt ggggtggaa caggagagac    7680 cctgggagag aaatgaagg cccgcttgaa ccagatgtcg gccctggagt tctactccta    7740
caaaaagtca ggcatcaccg aggtgtgcag agaagaggcc cgccgcgccc tcaaggacgg    7800
tgtggcaacg ggaggccatg ctgtgtcccg aggaagtgca aagctgagat ggttggtgga    7860
gcggggatac ctgcagccct acggaaaggt cattgatctt ggatgtggca gggggggctg    7920
gagttactac gccgccacca tccgcaaagt tcaagaagtg aaaggataca caaaaggagg    7980
ccctggtcat gaagaacccg tgttggtgca aagctatggg tggaacatag tccgtcttaa    8040
gagtggggtg gacgtctttc atatggcggc tgagccgtgt gacacgttgc tgtgtgacat    8100
```

```
aggtgagtca tcatctagtc ctgaagtgga agaagcacgg acgctcagag tcctctccat   8160
ggtgggggat tggcttgaaa aaagaccagg agccttttgt ataaaagtgt tgtgcccata   8220
caccagcact atgatggaaa ccctggagcg actgcagcgt aggtatgggg gaggactggt   8280
cagagtgcca ctctcccgca actctacaca tgagatgtac tgggtctctg gagcgaaaag   8340
caacaccata aaaagtgtgt ccaccacgag ccagctcctc ttggggcgca tggacgggcc   8400
taggaggcca gtgaaatatg aggaggatgt gaatctcggc tctggcacgc gggctgtggt   8460
aagctgcgct gaagctccca acatgaagat cattggtaac cgcattgaaa ggatccgcag   8520
tgagcacgcg gaaacgtggt tctttgacga gaaccaccca tataggacat gggcttacca   8580
tggaagctat gaggccccca cacaagggtc agcgtcctct ctaataaacg gggttgtcag   8640
gctcctgtca aaaccctggg atgtggtgac tggagtcaca ggaatagcca tgaccgacac   8700
cacaccgtat ggtcagcaaa gagttttcaa ggaaaaagtg gacactaggg tgccagaccc   8760
ccaagaaggc actcgtcagg ttatgagcat ggtctcttcc tggttgtgga aagagctagg   8820
caaacacaaa cggccacgag tctgtaccaa agaagagttc atcaacaagg ttcgcagcaa   8880
tgcagcatta gggcaatat ttgaagagga aaaagagtgg aagactgcag tggaagctgt   8940
gaacgatcca aggttctggg ctctagtgga caaggaaaga gagcaccacc tgagaggaga   9000
gtgccagagt tgtgtgtaca acatgatggg aaaaagagaa aagaaacaag gggaatttgg   9060
aaaggccaag ggcagccgcg ccatctggta tatgtggcta ggggctagat ttctagagtt   9120
cgaagccctt ggattcttga cgaggatca ctggatgggg agagagaact caggaggtgg   9180
tgttgaaggg ctgggattac aaagactcgg atatgtccta aagagatga gtcgcatacc   9240
aggaggaagg atgtatgcag atgacactgc tggctgggac acccgcatca gcaggtttga   9300
tctggagaat aagctctaa tcaccaacca aatggagaaa gggcacaggg ccttggcatt   9360
ggccataatc aagtacacat accaaaacaa agtggtaaag gtccttagac agctgaaaaa   9420
agggaaaaca gttatggaca ttatttcgag acaagaccaa ggggagcg acaagttgt   9480
cacttacgct cttaacacat ttaccaacct agtggtgcaa ctcattcgga atatggaggc   9540
tgaggaagtt ctagagatgc aagacttgtg gctgctgcgg aggtcagaga agtgaccaa   9600
ctggttgcag agcaacggat gggataggct caaacgaatg gcagtcagtg agatgattg   9660
cgttgtgaag ccaattgatg acaggtttgc acatgccctc aggttcttga atgatatggg   9720
aaaagttagg aaggacacac aagagtggaa accctcaact ggatgggaca ctgggaaga   9780
agttccgttt tgctcccacc acttcaacaa gctccatctc aaggacggga ggtccattgt   9840
ggttccctgc cgccaccaag atgaactgat tggccgggcc cgcgtctctc caggggcggg   9900
atggagcatc cgggagactg cttgcctagc aaaatcatat gcgcaaatgt ggcagctcct   9960
ttatttccat agaagggacc tccgactgat ggccaatgcc atttgttcat ctgtgccagt  10020
tgactgggtt ccaactggga gaactacctg gtcaatccat ggaaagggag aatggatgac  10080
cactgaagac atgcttgtgg tgtggaacag agtgtggatt gaggagaacg accacatgga  10140
agacaagacc ccagttacga aatggacaga cattccctat ttgggaaaaa gggaagactt  10200
gtggtgtgga tctctcatag ggacagacc gcgcaccacc tggctgaga acattaaaaa  10260
cacagtcaac atggtgcgca ggatcatagg tgatgaagaa aagtacatgg actacctatc  10320
cacccaagtt cgctacttgg gtgaagaagg gtctacacct ggagtgctgt aagcaccaat  10380
cttaatgttg tcaggcctgc tagtcagcca cagcttgggg aaagctgtgc agcctgtgac  10440
cccccagga gaagctggga aaccaagcct atagtcaggc cgagaacgcc atggcacgga  10500
```

```
agaagccatg ctgcctgtga gcccctcaga ggacactgag tcaaaaaacc ccacgcgctt    10560
ggaggcgcag gatgggaaaa gaaggtggcg accttcccca cccttcaatc tgggccctga    10620
actggagatc agctgtggat ctccagaaga gggactagtg gttagaggag acccccccgga   10680 aaacgcaaaa cagcatattg acgctgggaa agaccagaga ctccatgagt ttccaccacg    10740
ctggccgcca ggcacagatc gccgaatagc ggcggccggt gtggggaaat ccatg         10795
```

<210> SEQ ID NO 5
<211> LENGTH: 168
<212> TYPE: PRT
<213> ORGANISM: Artificial Sequence
<220> FEATURE:
<223> OTHER INFORMATION: Synthetic peptide
<300> PUBLICATION INFORMATION:
<308> DATABASE ACCESSION NUMBER: GenBank / KU926309.1
<309> DATABASE ENTRY DATE: 2016-03-21
<313> RELEVANT RESIDUES IN SEQ ID NO: (1)..(168)

<400> SEQUENCE: 5

```
Ala Glu Val Thr Arg Arg Gly Ser Ala Tyr Tyr Met Tyr Leu Asp Arg
1               5                   10                  15

Asn Asp Ala Gly Glu Ala Ile Ser Phe Pro Thr Thr Leu Gly Met Asn
            20                  25                  30

Lys Cys Tyr Ile Gln Ile Met Asp Leu Gly His Met Cys Asp Ala Thr
        35                  40                  45

Met Ser Tyr Glu Cys Pro Met Leu Asp Glu Gly Val Glu Pro Asp Asp
    50                  55                  60

Val Asp Cys Trp Cys Asn Thr Thr Ser Thr Trp Val Val Tyr Gly Thr
65                  70                  75                  80

Cys His His Lys Lys Gly Glu Ala Arg Arg Ser Arg Arg Ala Val Thr
                85                  90                  95

Leu Pro Ser His Ser Thr Arg Lys Leu Gln Thr Arg Ser Gln Thr Trp
            100                 105                 110

Leu Glu Ser Arg Glu Tyr Thr Lys His Leu Ile Arg Val Glu Asn Trp
        115                 120                 125

Ile Phe Arg Asn Pro Gly Phe Ala Leu Ala Ala Ala Ile Ala Trp
    130                 135                 140

Leu Leu Gly Ser Ser Thr Ser Gln Lys Val Ile Tyr Leu Val Met Ile
145                 150                 155                 160

Leu Leu Ile Ala Pro Ala Tyr Ser
                165
```

<210> SEQ ID NO 6
<211> LENGTH: 75
<212> TYPE: PRT
<213> ORGANISM: Artificial Sequence
<220> FEATURE:
<223> OTHER INFORMATION: Synthetic peptide
<300> PUBLICATION INFORMATION:
<308> DATABASE ACCESSION NUMBER: GenBank / KU926309.1
<309> DATABASE ENTRY DATE: 2016-03-21
<313> RELEVANT RESIDUES IN SEQ ID NO: (94)..(168)

<400> SEQUENCE: 6

```
Ala Val Thr Leu Pro Ser His Ser Thr Arg Lys Leu Gln Thr Arg Ser
1               5                   10                  15

Gln Thr Trp Leu Glu Ser Arg Glu Tyr Thr Lys His Leu Ile Arg Val
            20                  25                  30

Glu Asn Trp Ile Phe Arg Asn Pro Gly Phe Ala Leu Ala Ala Ala Ala
```

```
                35                  40                  45
Ile Ala Trp Leu Leu Gly Ser Ser Thr Ser Gln Lys Val Ile Tyr Leu
 50                  55                  60

Val Met Ile Leu Leu Ile Ala Pro Ala Tyr Ser
 65                  70                  75

<210> SEQ ID NO 7
<211> LENGTH: 504
<212> TYPE: PRT
<213> ORGANISM: Artificial Sequence
<220> FEATURE:
<223> OTHER INFORMATION: Synthetic peptide
<300> PUBLICATION INFORMATION:
<308> DATABASE ACCESSION NUMBER: GenBank / KU926309.1
<309> DATABASE ENTRY DATE: 2016-03-21
<313> RELEVANT RESIDUES IN SEQ ID NO: (169)..(672)

<400> SEQUENCE: 7

Ile Arg Cys Ile Gly Val Ser Asn Arg Asp Phe Val Glu Gly Met Ser
 1               5                  10                  15

Gly Gly Thr Trp Val Asp Val Val Leu Glu His Gly Gly Cys Val Thr
                20                  25                  30

Val Met Ala Gln Asp Lys Pro Thr Val Asp Ile Glu Leu Val Thr Thr
             35                  40                  45

Thr Val Ser Asn Met Ala Glu Val Arg Ser Tyr Cys Tyr Glu Ala Ser
 50                  55                  60

Ile Ser Asp Met Ala Ser Asp Ser Arg Cys Pro Thr Gln Gly Glu Ala
 65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Ala
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His Thr Ala Leu Ala Gly Ala
            260                 265                 270

Leu Glu Ala Glu Met Asp Gly Ala Lys Gly Arg Leu Ser Ser Gly His
        275                 280                 285

Leu Lys Cys Arg Leu Lys Met Asp Lys Leu Arg Leu Lys Gly Val Ser
    290                 295                 300
```

```
Tyr Ser Leu Cys Thr Ala Ala Phe Thr Phe Thr Lys Ile Pro Ala Glu
305                 310                 315                 320

Thr Leu His Gly Thr Val Thr Val Glu Val Gln Tyr Ala Gly Thr Asp
            325                 330                 335

Gly Pro Cys Lys Val Pro Ala Gln Met Ala Val Asp Met Gln Thr Leu
            340                 345                 350

Thr Pro Val Gly Arg Leu Ile Thr Ala Asn Pro Val Ile Thr Glu Ser
            355                 360                 365

Thr Glu Asn Ser Lys Met Met Leu Glu Leu Asp Pro Pro Phe Gly Asp
370                 375                 380

Ser Tyr Ile Val Ile Gly Val Gly Glu Lys Lys Ile Thr His His Trp
385                 390                 395                 400

His Arg Ser Gly Ser Thr Ile Gly Lys Ala Phe Glu Ala Thr Val Arg
            405                 410                 415

Gly Ala Lys Arg Met Ala Val Leu Gly Asp Thr Ala Trp Asp Phe Gly
            420                 425                 430

Ser Val Gly Gly Ala Leu Asn Ser Leu Gly Lys Gly Ile His Gln Ile
            435                 440                 445

Phe Gly Ala Ala Phe Lys Ser Leu Phe Gly Gly Met Ser Trp Phe Ser
450                 455                 460

Gln Ile Leu Ile Gly Thr Leu Leu Met Trp Leu Gly Leu Asn Thr Lys
465                 470                 475                 480

Asn Gly Ser Ile Ser Leu Met Cys Leu Ala Leu Gly Gly Val Leu Ile
            485                 490                 495

Phe Leu Ser Thr Ala Val Ser Ala
            500

<210> SEQ ID NO 8
<211> LENGTH: 18
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: C1

<400> SEQUENCE: 8

Trp Pro His Thr Gln Gly Pro Gly Cys Cys Gly Pro Gly Ser Trp Pro
1               5                   10                  15

Gly Gln

<210> SEQ ID NO 9
<211> LENGTH: 18
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: C2

<400> SEQUENCE: 9

Trp Pro His Thr Gln Gly Pro Gly Cys Cys Gly Pro Gly Leu Arg Gly
1               5                   10                  15

His Ala

<210> SEQ ID NO 10
<211> LENGTH: 20
<212> TYPE: PRT
```

```
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: C3

<400> SEQUENCE: 10

Trp Pro Trp Ile Gly Thr Gly Pro Gly Cys Cys Gly Pro Gly Lys Arg
1               5                   10                  15

Asn Ala Thr Pro
            20

<210> SEQ ID NO 11
<211> LENGTH: 20
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: C4

<400> SEQUENCE: 11

Trp Pro Trp Ile Gly Thr Gly Pro Gly Cys Cys Gly Pro Gly Lys Thr
1               5                   10                  15

Asp Ala Tyr Ser
            20

<210> SEQ ID NO 12
<211> LENGTH: 18
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: C5

<400> SEQUENCE: 12

Ala Gly Arg Arg Pro Gly Pro Gly Cys Cys Gly Pro Gly Ser Trp Pro
1               5                   10                  15

Gly Gln

<210> SEQ ID NO 13
<211> LENGTH: 18
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: C6

<400> SEQUENCE: 13

Ala Gly Arg Arg Pro Gly Pro Gly Cys Cys Gly Pro Gly Leu Arg Gly
1               5                   10                  15

His Ala

<210> SEQ ID NO 14
<211> LENGTH: 20
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
```

```
<223> OTHER INFORMATION: C7

<400> SEQUENCE: 14

Met Asp Ser Pro Ile Lys Gly Pro Gly Cys Cys Gly Pro Gly Lys Arg
1               5                   10                  15

Asn Ala Thr Pro
            20

<210> SEQ ID NO 15
<211> LENGTH: 20
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: C8

<400> SEQUENCE: 15

Met Asp Ser Pro Ile Lys Gly Pro Gly Cys Cys Gly Pro Gly Lys Thr
1               5                   10                  15

Asp Ala Tyr Ser
            20

<210> SEQ ID NO 16
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: C1 Binds to Active Site 2

<400> SEQUENCE: 16

Trp Pro His Thr Gln
1               5

<210> SEQ ID NO 17
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: C2 Binds to Active Site 2
<220> FEATURE:
<221> NAME/KEY: MISC_FEATURE
<223> OTHER INFORMATION: optionally includes an amino acid at the N-
      terminus, C-terminus or between two amino acids of the sequence

<400> SEQUENCE: 17

Trp Pro His Thr Gln
1               5

<210> SEQ ID NO 18
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: C3 Binds to Active Site 2

<400> SEQUENCE: 18

Trp Pro Trp Ile Gly Thr
```

```
<210> SEQ ID NO 19
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: C4 Binds to Active Site 2
<220> FEATURE:
<221> NAME/KEY: MISC_FEATURE
<223> OTHER INFORMATION: optionally includes an amino acid at the N-
      terminus, C-terminus or between two amino acids of the sequence

<400> SEQUENCE: 19

Trp Pro Trp Ile Gly Thr
1               5

<210> SEQ ID NO 20
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: C5 Binds to Active Site 2

<400> SEQUENCE: 20

Ala Gly Arg Arg Pro
1               5

<210> SEQ ID NO 21
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: C6 Binds to Active Site 2
<220> FEATURE:
<221> NAME/KEY: MISC_FEATURE
<223> OTHER INFORMATION: optionally includes an amino acid at the N-
      terminus, C-terminus or between two amino acids of the sequence

<400> SEQUENCE: 21

Ala Gly Arg Arg Pro
1               5

<210> SEQ ID NO 22
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: C7 Binds to Active Site 2

<400> SEQUENCE: 22

Met Asp Ser Pro Ile Lys
1               5

<210> SEQ ID NO 23
<211> LENGTH: 6
<212> TYPE: PRT
<213> ORGANISM: Artificial Sequence
```

```
<220> FEATURE:
<223> OTHER INFORMATION: Synthetic Peptide
<220> FEATURE:
<221> NAME/KEY: MISC_FEATURE
<223> OTHER INFORMATION: C8 Binds to Active Site 2

<400> SEQUENCE: 23

Met Asp Ser Pro Ile Lys
1               5

<210> SEQ ID NO 24
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: C1 Binds to Active Site 1

<400> SEQUENCE: 24

Ser Trp Pro Gly Gln
1               5

<210> SEQ ID NO 25
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: C2 Binds to Active Site 1

<400> SEQUENCE: 25

Leu Arg Gly His Ala
1               5

<210> SEQ ID NO 26
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: C3 Binds to Active Site 1

<400> SEQUENCE: 26

Lys Arg Asn Ala Thr Pro
1               5

<210> SEQ ID NO 27
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: C4 Binds to Active Site 1

<400> SEQUENCE: 27

Lys Thr Asp Ala Tyr Ser
1               5

<210> SEQ ID NO 28
<211> LENGTH: 5
<212> TYPE: PRT
```

```
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: C5 Binds to Active Site 1
<220> FEATURE:
<221> NAME/KEY: MISC_FEATURE
<223> OTHER INFORMATION: optionally includes an amino acid at the N-
      terminus, C-terminus or between two amino acids of the sequence

<400> SEQUENCE: 28

Ser Trp Pro Gly Gln
1               5

<210> SEQ ID NO 29
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: C6 Binds to Active Site 1
<220> FEATURE:
<221> NAME/KEY: MISC_FEATURE
<223> OTHER INFORMATION: optionally includes an amino acid at the N-
      terminus, C-terminus or between two amino acids of the sequence

<400> SEQUENCE: 29

Leu Arg Gly His Ala
1               5

<210> SEQ ID NO 30
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: C7 Binds to Active Site 1
<220> FEATURE:
<221> NAME/KEY: MISC_FEATURE
<223> OTHER INFORMATION: optionally includes an amino acid at the N-
      terminus, C-terminus or between two amino acids of the sequence

<400> SEQUENCE: 30

Lys Arg Asn Ala Thr Pro
1               5

<210> SEQ ID NO 31
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: C8 Binds to Active Site 1
<220> FEATURE:
<221> NAME/KEY: MISC_FEATURE
<223> OTHER INFORMATION: optionally includes an amino acid at the N-
      terminus, C-terminus or between two amino acids of the sequence

<400> SEQUENCE: 31

Lys Thr Asp Ala Tyr Ser
1               5

<210> SEQ ID NO 32
<211> LENGTH: 8
```

```
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: Bridge peptide

<400> SEQUENCE: 32

Gly Pro Gly Cys Cys Gly Pro Gly
1               5

<210> SEQ ID NO 33
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: P1

<400> SEQUENCE: 33

Cys Ser Trp Pro Gly Gln
1               5

<210> SEQ ID NO 34
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: P2

<400> SEQUENCE: 34

Cys Leu Arg Gly His Ala
1               5

<210> SEQ ID NO 35
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: X1

<400> SEQUENCE: 35

Cys Lys Arg Asn Ala Thr Pro
1               5

<210> SEQ ID NO 36
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: X2

<400> SEQUENCE: 36

Cys Lys Thr Asp Ala Tyr Ser
1               5

<210> SEQ ID NO 37
```

```
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 37

Ser Met Ala Gly Gly
1               5

<210> SEQ ID NO 38
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 38

Trp Pro Phe Phe Pro
1               5

<210> SEQ ID NO 39
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 39

Gly Pro Asn Ala Thr Pro
1               5

<210> SEQ ID NO 40
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 40

Trp Pro Trp Phe Gly Pro
1               5
```